(12) United States Patent
Kalpin

(10) Patent No.: US 8,810,394 B2
(45) Date of Patent: Aug. 19, 2014

(54) RESERVOIR MONITORING FOR IMPLANTABLE FLUID DELIVERY DEVICES

(75) Inventor: Scott L. Kalpin, Harris, MN (US)

(73) Assignee: Medtronic, Inc., Minneapolis, MN (US)

( * ) Notice: Subject to any disclaimer, the term of this patent is extended or adjusted under 35 U.S.C. 154(b) by 933 days.

(21) Appl. No.: 12/762,108

(22) Filed: Apr. 16, 2010

(65) Prior Publication Data

US 2011/0254686 A1 Oct. 20, 2011

(51) Int. Cl.
*G08B 21/00* (2006.01)

(52) U.S. Cl.
USPC .......... 340/540; 702/45; 702/50; 604/19; 604/27; 604/513; 604/67; 604/257; 604/892.1; 604/891.1; 604/890.1; 604/288.01; 604/531

(58) Field of Classification Search
USPC .......... 340/540; 604/97.01, 19, 27, 513, 67, 604/257, 531, 288.01, 890.1, 891.1, 892.1; 702/45, 47, 50, 138
See application file for complete search history.

(56) References Cited

U.S. PATENT DOCUMENTS

| | | |
|---|---|---|
| 4,373,527 A | 2/1983 | Fischell |
| 4,395,259 A | 7/1983 | Prestele et al. |
| 4,443,218 A | 4/1984 | DeCant, Jr. et al. |
| 4,486,190 A | 12/1984 | Reinicke |
| 4,561,298 A | 12/1985 | Pond |
| 4,718,430 A | 1/1988 | Holzer |
| 4,784,645 A | 11/1988 | Fischell |
| 4,840,064 A | 6/1989 | Fudim |
| 4,881,185 A | 11/1989 | Murakami et al. |
| 5,006,997 A | 4/1991 | Reich |
| 5,132,923 A | 7/1992 | Crawford et al. |
| 5,319,964 A | 6/1994 | Stephensen et al. |
| 5,472,420 A * | 12/1995 | Campbell ............ 604/67 |
| 5,507,737 A | 4/1996 | Palmskog |
| 5,904,666 A | 5/1999 | DeDecker et al. |
| 6,163,979 A * | 12/2000 | Oetjen et al. ............ 34/286 |

(Continued)

FOREIGN PATENT DOCUMENTS

| | | |
|---|---|---|
| EP | 0622615 A1 | 11/1994 |
| EP | 1649884 A1 | 4/2006 |

(Continued)

OTHER PUBLICATIONS

Office action for U.S. Appl. No. 12/762,064, mailed Aug. 12, 2011, 27 pages.

(Continued)

*Primary Examiner* — George Bugg
*Assistant Examiner* — Naomi Small
(74) *Attorney, Agent, or Firm* — Shumaker & Sieffert, P.A.

(57) ABSTRACT

A number of parameters related to the operation of a fluid delivery device are determined based on a pressure within the device sensed using a pressure sensor. In one example, the volume of therapeutic fluid added to or removed from a reservoir of a fluid delivery device is determined based on a sensed pressure of the reservoir. In another example, the volume of therapeutic fluid added to or removed from the reservoir is determined based on a sensed pressure of a refill port assembly of the device. In another example, an initial temperature of the reservoir as a therapeutic fluid is removed from the reservoir is estimated based on a sensed pressure within the device. In another example, a temperature of a therapeutic fluid added to the reservoir is estimated based on a sensed pressure within the device.

39 Claims, 13 Drawing Sheets

(56) References Cited

U.S. PATENT DOCUMENTS

| | | |
|---|---|---|
| 6,302,864 B1 | 10/2001 | Nowosielski |
| 6,315,769 B1 | 11/2001 | Peer et al. |
| 6,321,597 B1 | 11/2001 | Demers et al. |
| 6,542,848 B1 | 4/2003 | Neeser et al. |
| 6,562,001 B2 | 5/2003 | Lebel et al. |
| 6,740,059 B2 | 5/2004 | Flaherty |
| 6,810,308 B2 | 10/2004 | Shajii et al. |
| 6,939,111 B2 | 9/2005 | Huitt et al. |
| 7,054,782 B2 | 5/2006 | Hartlaub |
| 7,137,964 B2 | 11/2006 | Flaherty |
| 7,206,715 B2 | 4/2007 | Vanderveen et al. |
| 7,694,591 B2 | 4/2010 | Leibfried |
| 7,890,273 B2 * | 2/2011 | Lovell et al. .................... 702/45 |
| 8,313,308 B2 * | 11/2012 | Lawless et al. ............... 417/44.2 |
| 2002/0087116 A1 | 7/2002 | Hartlaub |
| 2002/0161328 A1 | 10/2002 | Rogers |
| 2003/0084589 A1 * | 5/2003 | Chowdhury et al. ........... 34/403 |
| 2004/0249336 A1 | 12/2004 | Faries et al. |
| 2004/0260233 A1 | 12/2004 | Garibotto et al. |
| 2005/0033197 A1 * | 2/2005 | Cottler .......................... 600/573 |
| 2005/0075624 A1 | 4/2005 | Miesel |
| 2005/0187515 A1 | 8/2005 | Varrichio et al. |
| 2005/0214129 A1 * | 9/2005 | Greene et al. .................... 417/18 |
| 2006/0089619 A1 | 4/2006 | Ginggen |
| 2006/0149220 A1 | 7/2006 | Ullestad et al. |
| 2006/0219017 A1 | 10/2006 | Silverbrook et al. |
| 2006/0276744 A1 | 12/2006 | Falk |
| 2007/0068528 A1 | 3/2007 | Bohm et al. |
| 2007/0106280 A1 | 5/2007 | Utard et al. |
| 2007/0225924 A1 * | 9/2007 | Hashizume et al. ............ 702/50 |
| 2007/0239381 A1 | 10/2007 | Ginggen et al. |
| 2007/0250045 A1 | 10/2007 | Trieu |
| 2007/0255259 A1 | 11/2007 | Miesel |
| 2008/0125702 A1 * | 5/2008 | Blischak et al. ................. 604/67 |
| 2008/0243093 A1 | 10/2008 | Kalpin et al. |
| 2009/0082757 A1 * | 3/2009 | Rogers et al. .............. 604/891.1 |
| 2009/0270844 A1 | 10/2009 | Seeley et al. |
| 2010/0125246 A1 | 5/2010 | Kalpin |
| 2010/0137842 A1 | 6/2010 | Gibson |
| 2010/0288788 A1 * | 11/2010 | Ophardt ........................... 222/1 |

FOREIGN PATENT DOCUMENTS

| | | |
|---|---|---|
| EP | 1839635 A1 | 10/2007 |
| WO | 0072900 A1 | 12/2000 |
| WO | 0228454 A2 | 4/2002 |
| WO | 03068049 A2 | 8/2003 |
| WO | 2007041471 A2 | 4/2007 |
| WO | 2008121421 A1 | 10/2008 |
| WO | 2009137780 A2 | 11/2009 |
| WO | 2010/059588 A1 | 5/2010 |

OTHER PUBLICATIONS

Notification of Transmittal of the International Search Report and the Written Opinion of the International Searching Authority for patent application No. PCT/US2011/023086, mailed Oct. 12, 2011, 16 pages.

Response to office action for U.S. Appl. No. 12/762,064, filed Nov. 11, 2011, 26 pages.

Final office action for U.S. Appl. No. 12/762,064, dated Mar. 5, 2012, 27 pages.

International Search Report and Written Opinion of PCT/US2011/023096, dated Jul. 8, 2011, 10 pp.

U.S. Appl. No. 12/762,064, filed Apr. 16, 2010, Nelson Konen et al.

U.S. Appl. No. 12/762,121, filed Apr. 16, 2010, Kalpin.

Office Action from U.S. Appl. No. 12/762,121 dated Mar. 7, 2014, 22 pp.

Office action from U.S. Appl. No. 12/762,121, dated Aug. 6, 2013, 21 pp.

Watsham et al., excerpt from Quantitative Methods in Finance, 1997, p. 103.

Response to Office Action dated Aug. 6, 2013, from U.S. Appl. No. 12/762,121, filed Nov. 6, 2013, 6 pp.

* cited by examiner

RESERVOIR MONITORING FOR IMPLANTABLE FLUID DELIVERY DEVICES

TECHNICAL FIELD

This disclosure relates generally to implantable medical devices and, more particularly, to implantable fluid delivery devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to the delivery site in the patient.

SUMMARY

In general, this disclosure describes techniques for determining a number of parameters related to the operation of a fluid delivery device, e.g., an implantable drug infusion device, based on a pressure within the device sensed using a pressure sensor. In some examples, the parameters can be used to monitor a fill status or volume of a reservoir in the fluid delivery device.

In one example, a method includes sensing a pressure within a fluid delivery device using a pressure sensor as a therapeutic fluid is added to or removed from a reservoir of the device, estimating a pressure of the reservoir based on the sensed pressure, and determining a volume of the fluid added to or removed from the reservoir based on the sensed pressure and the estimated pressure of the reservoir.

In another example, a fluid delivery system includes an implantable fluid delivery device and a processor. The implantable fluid delivery device includes a reservoir configured to store a therapeutic fluid and a pressure sensor configured to sense one or more pressures within the fluid delivery device. The processor is configured to sense a pressure within the fluid delivery device using the pressure sensor as a therapeutic fluid is added to or removed from the reservoir, estimate a pressure of the reservoir based on the sensed pressure, and determine a volume of the fluid added to or removed from the reservoir based on the sensed pressure and the estimated pressure of the reservoir.

In another example, a computer-readable storage medium includes instructions for causing a programmable processor in an implantable fluid delivery system to sense a pressure within a fluid delivery device using a pressure sensor as a therapeutic fluid is added to or removed from a reservoir of the device, estimate a pressure of the reservoir based on the sensed pressure, and determine a volume of the fluid added to or removed from the reservoir based on the sensed pressure and the estimated pressure of the reservoir.

In another example, a system includes means for sensing a pressure within a fluid delivery device using a pressure sensor as a therapeutic fluid is added to or removed from a reservoir of the device, means for estimating a pressure of the reservoir based on the sensed pressure, and means for determining a volume of the fluid added to or removed from the reservoir based on the sensed pressure and the estimated pressure of the reservoir.

In another example, a method includes sensing a pressure within a fluid delivery device using a pressure sensor as a therapeutic fluid is added to or removed from a reservoir of the device, estimating an initial temperature of the reservoir as the therapeutic fluid is added or removed based on the sensed pressure, estimating a temperature of the therapeutic fluid based on the sensed pressure, determining an estimated pressure of the reservoir based on the estimated initial temperature of the reservoir and the estimated temperature of the therapeutic fluid, and determining a volume of the fluid added to or removed from the reservoir based on the sensed pressure and the estimated pressure of the reservoir.

The details of one or more examples disclosed herein are set forth in the accompanying drawings and the description below. Other features, objects, and advantages will be apparent from the description and drawings, and from the claims.

DETAILED DESCRIPTION

Figure 1:
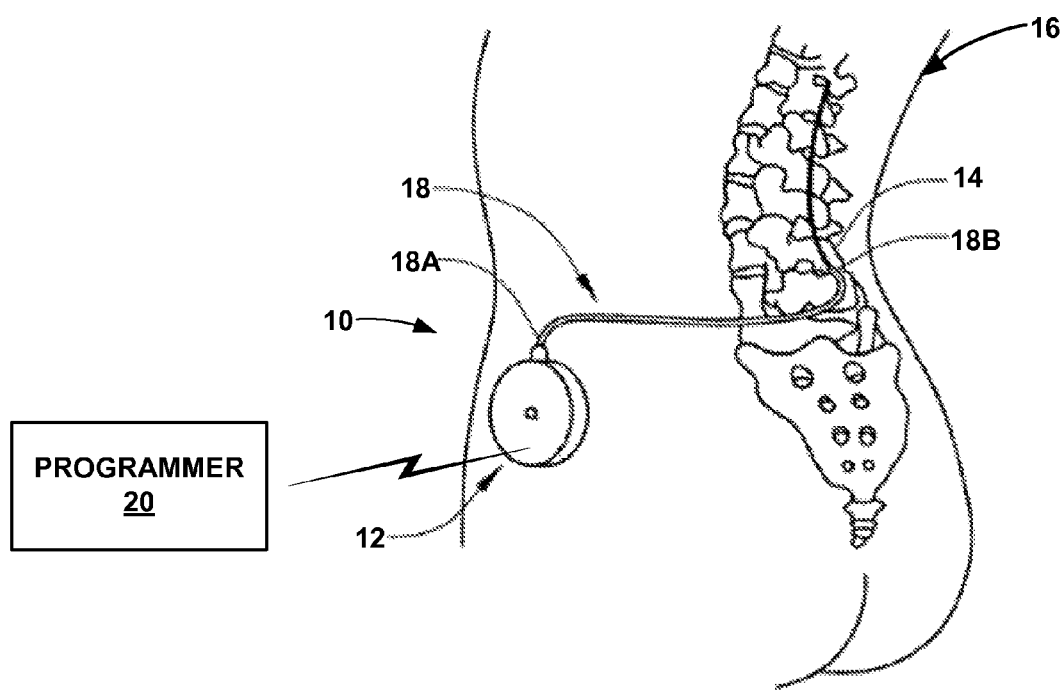
FIG. 1 is a conceptual diagram illustrating an example of a fluid delivery system including an implantable fluid delivery device configured to deliver a therapeutic fluid to a patient via a catheter.

This application is related to U.S. patent application Ser. No. 12/619,145, filed Nov. 16, 2009, which claims the benefit of U.S. Provisional Application Ser. No. 61/116,309, filed Nov. 20, 2008, both of which applications are incorporated herein by this reference. This application is also related to U.S. patent application Ser. No. 12/199,536, filed Aug. 27, 2008, which claims the benefit of U.S. Provisional Application Ser. No. 60/975,286, filed Sep. 26, 2007, both of which applications are incorporated herein by this reference.

It is generally useful for the safe and intended operation of IMD 12 to know the fill status of the reservoir(s) of the device, e.g. total volume of therapeutic fluid in the reservoir and/or the fill state of the reservoir as empty, filling, or full. For example, it may be useful to verify that a clinician has correctly accessed a refill port of IMD 12 and is actually filling the reservoir with therapeutic fluid to prevent an unintended injection of the fluid into a tissue pocket within patient 16. Additionally, it may be generally useful to monitor the fill status of the reservoir of IMD 12 to detect unexpected changes in the amount of fluid in the device. An unexpected change in fluid volume may occur when patient 16 or another person, outside of a clinical environment, attempts to access the refill port of the reservoir of IMD 12 to remove therapeutic fluid from the device. Another cause of unexpected changes in fluid volume in the reservoir may be valve leakage or pump stroke volume variation. Unexpected changes in reservoir volume may affect the desired operation of the device by causing potentially underdosing or overdosing of patient 16 with the therapeutic fluid delivered by IMD 12. Underdosing of patient 16 may be of particular interest in cases where rapidly reducing the amount of therapeutic fluid delivered by IMD 12 to the patient may cause withdrawal symptoms. Device awareness of reservoir fill status is important for these and other reasons related to the proper operation of IMD 12 and the efficacious delivery of therapy to patient 16 by the device.

Although different mechanisms are capable of determining the volume of therapeutic fluid in the reservoir of IMD 12, one convenient and economical method is to employ a pressure sensor that monitors pressure within the device over time. Generally speaking, the volume of the reservoir of IMD 12 may be extrapolated from the sensed pressure. However, the relationship between sensed pressure and reservoir fluid volume varies with temperature, which may not be constant. For example, in the event the temperature of a therapeutic fluid added to the reservoir of IMD 12 is not the same as the reservoir temperature, fluid volume will depend both on pressure changes and temperature changes. Therefore, it also may be necessary, in temperature-dependent applications, to determine one or more temperatures related to filling the reservoir of IMD 12 with a therapeutic fluid. In particular, it may be necessary for the proper monitoring of reservoir volume to determine the temperature of the reservoir of IMD 12, which may, in some examples, be equated to the temperature of the gas propellant used to pressurize the reservoir of the device and the temperature of therapeutic fluid added to the reservoir.

One challenge with extrapolating reservoir volume from pressure in temperature-dependent applications is that the temperatures of the reservoir IMD 12 and the therapeutic fluid are unknown. Both temperatures may be measured by employing additional sensors, such as temperature sensors to directly measure temperature. However, incorporation of additional sensors may add cost and complexity to IMD 12. Measuring temperatures directly may also complicate the process of refilling IMD 12 with therapeutic fluid, because, e.g., a user, such as a clinician may be required to measure and then enter the fluid temperature into programmer 20 to be transmitted to IMD 12.

In view of the foregoing challenges with the proper and safe operation of IMD 12, or other similar devices, techniques are disclosed in which the temperature and pressure dependent volume of fluid in the reservoir of the device can be estimated based only on a sensed pressure. In this manner, in some examples, volume and/or fill status can be determined without directly measuring temperature. Instead, pressure measurements can be used to indirectly determine temperature. It is noted, however, that in some examples a temperature sensor may be employed to measure temperature directly either as a direct input to determination of reservoir volume and/or fill status, or to verify the estimated temperature values.

As described in detail with reference to the following examples, reservoir volume estimates may be calculated by extrapolating not only fluid refill (removal) rate from a sensed pressure, but also estimating the initial temperature of the reservoir of IMD 12 and the temperature of the therapeutic fluid from the same pressure measurements in order to adjust the sensed pressure for the effects of varying temperature. The initial temperature of the reservoir of IMD 12 corresponds generally to the temperature of the reservoir at the beginning of a fill or refill operation, in which an empty or nearly empty reservoir is filled therapeutic fluid. The temperature of the therapeutic fluid is the temperature of the fluid as it is added to the reservoir of IMD 12 during a fill or refill operation. The initial temperature of the reservoir of IMD 12 and the temperature of the therapeutic fluid are estimated by identifying inflection points in the pressure profile of the reservoir over time during a refill operation, from which temperature can be estimated based on a known temperature-pressure characteristic for the device. Particular techniques for determining the fill status of IMD 12 will be described in greater detail with reference to FIGS. 4-11. However, an example fluid delivery system including an implantable fluid delivery device and external programmer will first be described with reference to FIGS. 1-3.

FIG. 1 is a conceptual diagram illustrating an example of a therapy system 10, which includes implantable medical device (IMD) 12, catheter 18, and external programmer 20. IMD 12 is connected to catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic fluid. In still other examples, IMD 12 may be external to patient 16 with a percutaneous catheter connected between IMD 12 and the target delivery site within patient 16.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics. Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to targets proximate to spinal cord 14. IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IMD 12 by wireless telemetry. For example, programmer 20 may be a clinician programmer that the clinician uses to communicate with IMD 12 and program therapy delivered by the IMD. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

Figure 2:
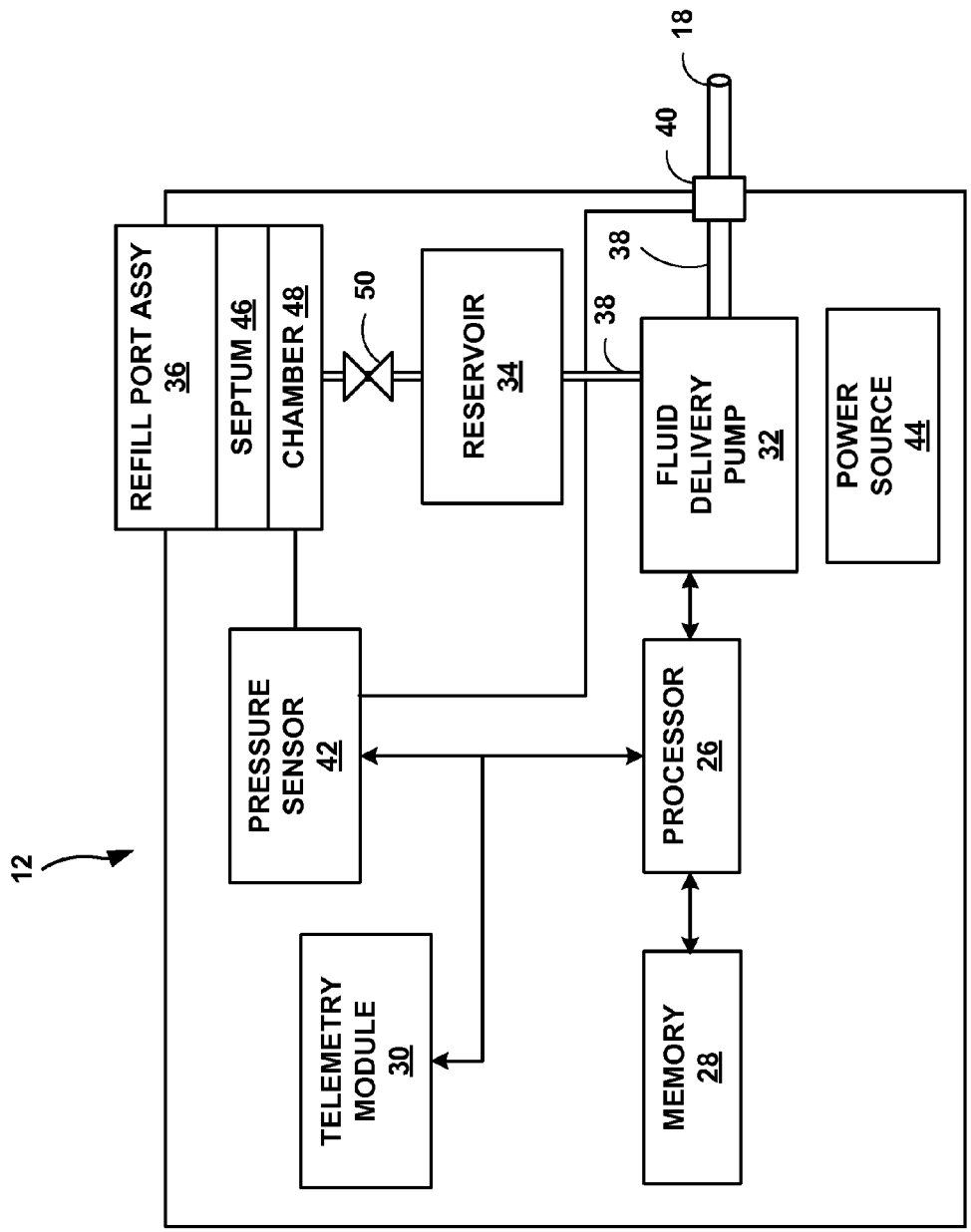
FIG. 2 is functional block diagram illustrating an example of the implantable fluid delivery device of FIG. 1.

As described in greater detail below with reference to FIGS. 4-11, IMD 12, alone or in cooperation with programmer 20 or another external device communicatively connected to IMD 12, is configured to determine a number of parameters related to the operation of the device based on a pressure within the device sensed using a pressure sensor. In some examples, the parameters determined by IMD 12 based sensed pressure can be used to monitor a fill status or volume of a reservoir of the device. In other examples, IMD 12 may be configured to estimate one or more temperatures based sensed pressure independent of any fill status or reservoir volume monitoring FIG. 2 is a functional block diagram illustrating components of an example of IMD 12, which includes processor 26, memory 28, telemetry module 30, fluid delivery pump 32, reservoir 34, refill port assembly 36, internal tubing 38, catheter access port assembly 40, pressure sensor 42, and power source 44. Processor 26 is communicatively connected to memory 28, telemetry module 30, fluid delivery pump 32, and pressure sensor 42. Fluid delivery pump 32 is connected to reservoir 34 and internal tubing 38. Reservoir 34 is connected to refill port assembly 36, which includes septum 46, chamber 48, and valve 50. Catheter access port assembly 40 is connected to internal tubing 38 and catheter 18. IMD 12 also includes power source 44, which is configured to deliver operating power to various components of the IMD.

During operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from reservoir 30 via catheter 18. The programs may further specify a schedule of different therapeutic fluid rates and other parameters by which IMD 12 delivers therapy to patient 16.

In general, a therapy program stored on memory 28 and executed by processor 26 defines one or more therapeutic fluid doses to be delivered from reservoir 34 to patient 16 through catheter 18 by IMD 12. A dose of therapeutic fluid generally refers to a total amount of therapeutic fluid, e.g., measured in milligrams or other volumetric units delivered over a total amount of time, e.g., per day or twenty-four hour period. The amount of therapeutic fluid in a dose may convey to a caregiver an indication of the probable efficacy of the fluid and the possibility of side effects. In general, a sufficient amount of the fluid should be administered in order to have a desired therapeutic effect, such as pain relief. However, the amount of the therapeutic fluid delivered to the patient should be limited to a maximum amount, such as a maximum daily amount, in order not to avoid potential side effects. Therapy program parameters specified by a user, e.g., via programmer 20 may include fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g. a twenty-four hour period. The therapeutic fluid rate refers to the amount, e.g. in volume, of therapeutic fluid delivered over a unit period of time, which may change over the course of the day as IMD 12 delivers the dose of fluid to patient 16. For example, IMD 12 may be programmed to deliver therapeutic fluid to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). The therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via external programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 is also programmed according to a therapy schedule such that the fluid is delivered at different rates at different times during the day, which may be stored in the device memory, e.g., as a look-up table associating different fluid rates at different times during the day. Upon instruction from processor 26, fluid delivery pump 32 draws fluid from reservoir 34 and pumps the fluid through internal tubing 38 to catheter 18 through which the fluid is delivered to patient 16 to effect one or more of the treatments described above in accordance with the program stored on memory 28. Internal tubing 38 is a segment of tubing or a series of cavities within IMD 12 that run from reservoir 34, around or through fluid delivery pump 32 to catheter access port 40.

Fluid delivery pump 32 can be any mechanism that delivers a therapeutic fluid in some metered or other desired flow dosage to the therapy site within patient 16 from reservoir 30 via implanted catheter 18. In one example, fluid delivery pump 32 is a squeeze pump that squeezes internal tubing 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26. Fluid delivery pump 32 may also be an axial pump, a centrifugal pump, a pusher plate, a piston-driven pump, or other means for moving fluid through internal tubing 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

Periodically, fluid may need to be supplied percutaneously to reservoir 34 because all of a therapeutic fluid has been or will be delivered to patient 16, or because a clinician wishes to replace an existing fluid with a different fluid or similar fluid with different concentrations of therapeutic ingredients. Refill port assembly 36 may therefore generally include a self-sealing membrane to prevent loss of therapeutic fluid delivered to reservoir 30 via refill port 26. For example, after a percutaneous delivery system, e.g., a hypodermic needle, penetrates the membrane of refill port assembly 36, the membrane may seal shut when the needle is removed from refill port 36.

In particular, refill port assembly 36 of IMD 12 includes septum 46, port chamber 48, and valve 50. Septum 46 is a self-sealing membrane that seals port chamber 48 relative to an exterior of the housing of IMD 12. Port chamber 48, in turn, is in fluid communication with reservoir 34 via valve 50, which may be actuated to selectively fluidly connect the port chamber and the reservoir. Valve 50 may include, e.g., a check valve configured to be actuated at a target fluid pressure to allow therapeutic fluid to pass from port chamber 48 to reservoir 34, while restricting flow back from the reservoir to the port chamber. A hypodermic needle may percutaneously deliver a therapeutic fluid to refill port assembly 36, and, in particular, through septum 46 and into port chamber 48, as part of a refilling operation of reservoir 34. The therapeutic fluid may then be pushed from port chamber 48 through valve 50 to reservoir 34. In one example, the pressure in reservoir 34 is less than ambient atmospheric pressure such that the hypodermic needle need not be actuated by a clinician, but, rather, the ambient atmospheric pressure initiates and sustains the flow of therapeutic fluid into the reservoir. In other examples, however, pressure may be placed on a plunger of a syringe of the hypodermic needle to exert a higher pressure to push the therapeutic fluid into reservoir 34 through refill port assembly 36.

Generally speaking, in examples according to this disclosure, reservoir 34 includes a flexible chamber, e.g. a bellows, the pressure of which is maintained via a propellant, e.g. a propellant gas. The propellant gas acts as a pressure-providing means to the chamber of reservoir 34, which compresses the flexible structure to discharge the therapeutic fluid stored in the reservoir. In some examples, the propellant gas used to pressurize and drive reservoir 34 of IMD 12 may be a fluid that is in phase change between a liquid state and a gas state when, e.g., in equilibrium between phases at around 35-37 degrees Celsius which is the usual temperature range of the body of patient 16. The propellant gas employed in examples of IMD 12 may comprise at least one of butane, perfluorohexane, or perfluoropentane.

As already noted, although IMD 12 is shown in the example of FIG. 2 as including a single reservoir 34 with corresponding single refill port assembly 36, in other examples, IMD 12 may include a number of reservoirs with a number of refill port assemblies for delivering one or more therapeutic fluids to patient 16. Additionally, IMD 12 may be constructed without a separate reservoir chamber, in which case port chamber 48 of refill port assembly 36 may be in direct fluid communication with catheter 18, via valve 50, such that a therapeutic substance infused from a needle through septum 46 into the port chamber will be delivered directly to a target area of patient 16 through the catheter.

Regardless of the particular configuration of IMD 12, the device may include, as shown in the example of FIG. 2, pressure sensor 42 operatively situated to sense pressures somewhere in or between refill port assembly 36 and reservoir 34. Generally speaking, pressure sensor 42 may detect pressures in refill port assembly 36 or reservoir 34. In one example, pressure sensor 42 detects pressure in port chamber 48, from which the pressure of reservoir 34 may be determined. For example, the pressure of port chamber 48 may be approximately equal to the pressure of reservoir 34 plus or minus the drop across any fluidic restriction between port and reservoir. In other examples, pressure sensor 42 may be arranged to detect pressure in reservoir 34 directly. Pressure sensor 42 is communicatively connected to processor 26 to transmit pressure-related information to the processor for analysis and storage on memory 28 in order to, e.g., determine a fill status of reservoir 34.

As will be described in greater detail with reference to the example method of FIG. 4, in one example, processor 26 may be configured to receive a sensed pressure from pressure sensor 42. Processor 26 estimates the pressure within reservoir 34 based on the sensed pressure. Processor 26 determines a volume of fluid added to or removed from reservoir 34 based on the pressure sensed by pressure sensor 42 and the pressure of the reservoir estimated by processor 26. The volume of fluid added to or removed from reservoir 34 determined by processor 26 may be, e.g., stored in memory 28. In some examples, processor 26 may also combine the fluid volume added to or removed from reservoir 34 with a starting volume of therapeutic fluid in the reservoir to determine a fill status of the reservoir, e.g., to determine one of a total volume of therapeutic fluid in the reservoir, an indication that the reservoir is empty, an indication that reservoir is being filled, or an indication that the reservoir is full.

Processor 26 may also trigger one or more actions based on the information transmitted by pressure sensor 42 including generation of an empty or full reservoir alarm or displaying the fill status of reservoir 34 on an external device including, e.g., programmer 20 by transmitting reservoir volume and/or fill status information to the programmer via telemetry module 30. Alarms triggered by processor 26, or another component of IMD 12 or another device, e.g. programmer 20, may generally include audible, tactile, and/or visual alerts. For example, a reservoir empty or full state alarm may include audible alerts issued by programmer 20 or another external device associated with therapy system 10. In another example, a reservoir fill status alarm includes IMD 12 vibrating within the body of patient 16, thereby providing a tactile alert. In other examples, the alarm includes text or graphical messages delivered to patient 16 and/or a clinician via text message or e-mail from programmer 20 or another electronic device communicatively connected to IMD 12 and/or programmer 20, thereby providing a visual alert.

In some examples, processor 26 may be configured to prompt operation of a display of external programmer 20, or another display device incorporated in or communicatively connected to IMD 12, based upon pressure-related information generated and signaled by pressure sensor 42. For example, processor 26 may be configured to control telemetry module 30 to transmit commands to a processor of programmer 20 to prompt a display of the programmer to present a user with an indicator of fluid addition or removal upon determining that the pressure sensed by pressure sensor 42 (or as otherwise indicated by information signaled from the pressure sensor) is indicative of fluid being withdrawn from or added to reservoir 34. In addition, the pressure sensed by pressure sensor 42 may be interpreted by processor 26 as indicating that reservoir 34 is empty or full, in which case the processor may prompt programmer 20 to display an indication of empty or full to the user. In other examples, the information from pressure sensor 42 may be employed to calculate the volume of therapeutic fluid in reservoir 34.

Pressure sensor 42 may be any device capable of sensing and signaling information indicative of pressure characteristics associated with port chamber 48, the passage between the port chamber and reservoir 34, or the reservoir. For example, pressure sensor 42 may be a capacitive measurement device which determines pressure by measuring the change in capacitance of a flexible membrane attached but insulated from a conductive, gas-filled cavity due to deflections caused by pressure applied over the flexible membrane. Alternatively, pressure sensor 42 may be a sensor that utilizes the piezo-electric effect or resistive change due to metallic strain in order to measure pressure applied. Regardless of the specific manner in which pressure sensor 42 measures pressure, in some examples, pressure sensor 42 is adapted to generate a signal indicative of a pressure of port chamber 48, from which the pressure of reservoir 34 may be determined based on a known fluid restriction constant for refill port assembly 36. In other examples, pressure sensor 42 may be adapted to generate a signal indicative of a pressure of reservoir 34 directly.

Pressure sensor 42 may be electronically coupled to processor 26, or a processor of another device, in a variety of ways. For example, electrical wiring (not shown) can provide the desired electrical connection. Alternatively, a wireless link may be provided between pressure sensor 42 and the processing device and/or display device selected.

In addition to measuring pressure in refill port assembly 36 and reservoir 34, pressure sensor 42 or additional pressure sensors may be employed to detect pressure conditions in other parts of IMD 12. For example, pressure sensor 42 may be connected to catheter access port assembly 40 to detect pressure changes between a port chamber and a lumen of catheter 18. Such pressure measurements may be employed by processor 26, in some examples, to detect malfunctions in catheter 18 by analyzing the pressure pulse induced in a lumen of the catheter when a pulse of therapeutic fluid is delivered through the catheter to patient 16 by pump 32.

Memory 28 of IMD 12 may store one or more programs including instructions for execution by processor 26, including, e.g., therapy programs, historical therapy programs, timing programs for delivery of fluid from reservoir 34 to catheter 18, pressure information provided by pressure sensor 42, fill status of reservoir 34, and any other information regarding therapy of patient 16. A program may indicate the bolus size or flow rate of the drug, and processor 26 may accordingly deliver therapy. A program may also indicate the frequency at which pressure sensor 42 is commanded to measure pressure within reservoir 34 of IMD 12 and define the manner by which processor 26 extrapolates the fill status and/or volume of therapeutic fluid in the reservoir.

Memory 28 may include separate memories for storing instructions, patient information, therapy parameters (e.g., grouped into sets referred to as "dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 28 stores program instructions that, when executed by processor 26, cause IMD 12 and processor 26 to perform the functions attributed to them in this disclosure.

At various times during the operation of IMD 12 to treat patient 16, communication to and from IMD 12 may be necessary to, e.g., change therapy programs, adjust parameters within one or more programs, configure or adjust a particular bolus, send or receive reservoir volume or pressure information or fill status, or to otherwise download information to or from IMD 12. Processor 26 therefore controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively according to, e.g., the 802.11 or Bluetooth specification sets, infrared (IR) communication according to the IRDA specification set, or other standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 3:
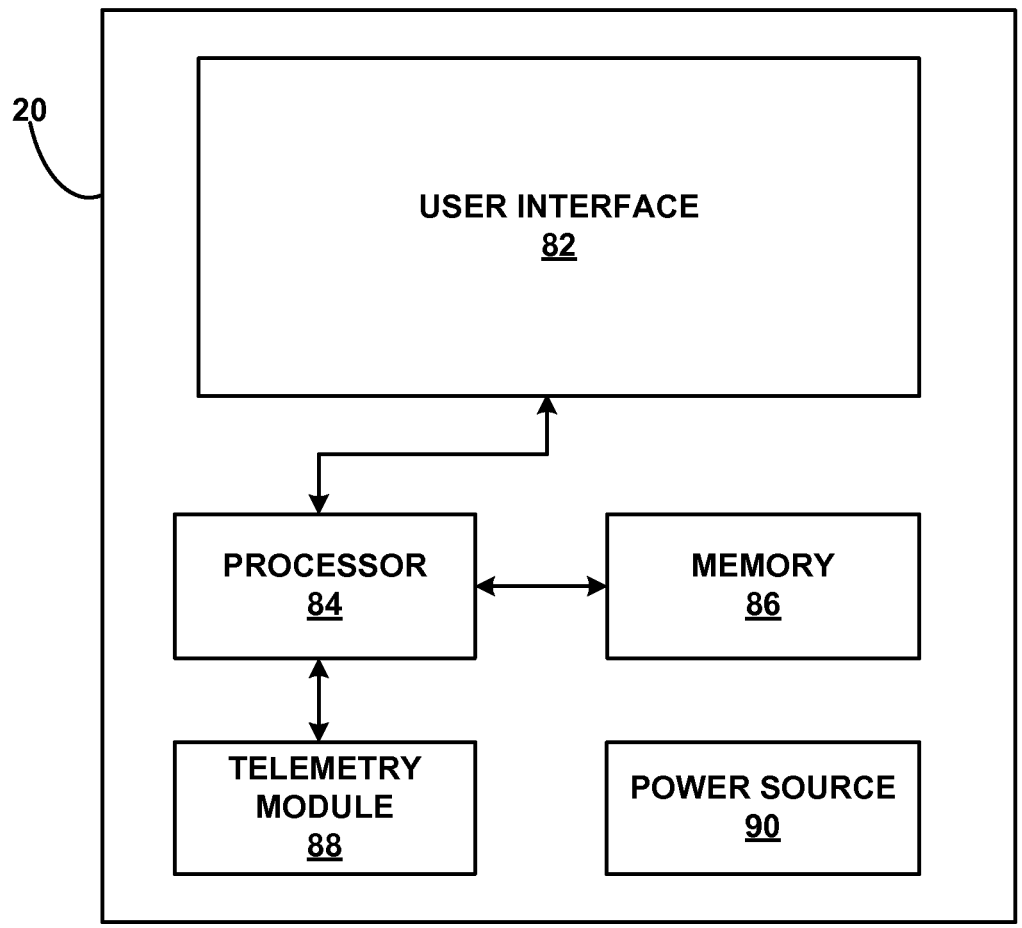
FIG. 3 is a functional block diagram illustrating an example of the external programmer of FIG. 1.

FIG. 3 is a functional block diagram illustrating various components of external programmer 20 for IMD 12. As shown in FIG. 3, external programmer 20 includes user interface 82, processor 84, memory 86, telemetry module 88, and power source 90. A clinician or patient 16 interacts with user interface 82 in order to manually change the parameters of a dosing program, change dosing programs within a group of programs, view therapy information, view historical therapy programs, view pressure information provided by pressure sensor 42 and/or volume and fill status of reservoir 34, establish new therapy regimens, or otherwise communicate with IMD 12 or view or edit programming information.

User interface 82 may include a screen and one or more input buttons, as discussed in greater detail below, that allow external programmer 20 to receive input from a user. Alternatively, user interface 82 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, e.g. an alarm indicating a refill state, e.g. empty or full, of reservoir 34, programmer 20 may further include one or more audio speakers, voice synthesizer chips, piezoelectric buzzers, or the like.

Input buttons for user interface 82 may include a touch pad, increase and decrease buttons, emergency shut off button, and other buttons needed to control the therapy, as described above with regard to patient programmer 20. Processor 84 controls user interface 82, retrieves data from memory 86 and stores data within memory 86. Processor 84 also controls the transmission of data through telemetry module 88 to IMD 12. The transmitted data may include therapy program information specifying various drug delivery program parameters. Memory 86 may include operational instructions for processor 84 and data related to therapy for patient 16.

User interface 82 may be configured to present therapy program information to the user. User interface 82 enables a user to program IMD 12 in accordance with one or more dosing programs, therapy schedules, or the like. For example, a user such as a clinician, physician or other caregiver may input patient information, drug information including expiration time of the drug, therapy schedules, priming information, bridging information, drug/IMD implant location information, or other information to programmer 20 via user interface 82. In addition, user interface 82 may display therapy program information as graphical bar graphs or charts, numerical spread sheets, or in any other manner in which information may be displayed. Further, user interface 82 may present nominal or suggested therapy parameters that the user may accept via user interface 82.

When programmer 20 is configured for use by a clinician, user interface 82 may be used to transmit initial programming information to IMD 12 including hardware information for system 10, e.g. the type of catheter 18, the position of catheter 18 within patient 16, a baseline orientation of at least a portion of IMD 12 relative to a reference point, and software information related to therapy delivery and operation of IMD 12, e.g. therapy parameters of therapy programs stored within IMD 12 or within programmer 20, the type and amount, e.g., by volume of therapeutic fluid(s) delivered by IMD 12 and any other information the clinician desires to program into IMD 12. The clinician may use programmer 20 during a programming session to define one or more therapy programs by which IMD 12 delivers therapy to patient 16, in which case patient 16 may provide feedback to the clinician during the programming session as to efficacy of a program being evaluated or desired modifications to the program. Programmer 20 may assist the clinician in the creation/identification of therapy programs by providing a methodical system of identifying potentially beneficial therapy parameters.

Programmer 20 may also be configured for use by patient 16. When configured as a patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

User interface 82 of programmer 20 may also be configured to display pressure information provided by pressure sensor 42 of IMD 12 and/or volume and fill status of reservoir 34 determined from such pressure information. For example, user interface 82 may display a gauge, e.g., as used in a car for gas or a cell phone for battery life, to indicate to a user the volume of therapeutic fluid left in reservoir 34 of IMD 12 during normal operation of the device to deliver the fluid to patient 16. User interface 82 may also display a graphical representation of the volume of fluid in reservoir 34 during a refill operation. For example, user interface 82 may display a graph of volume versus time, in which the changing volume of fluid in reservoir 34 is represented over the time of the refill. Similarly, user interface 82 may also display graphical representations of other parameters determined based on signals generated by pressure sensor 42 including, e.g., pressure in the reservoir, as well as one or more temperatures related to filling the reservoir with a therapeutic fluid.

In some examples, processor 84 of programmer 20 may be employed instead of or in conjunction with processor 26 of IMD 12 to determine a fill status of reservoir 34. In one example, processor 84 is configured to receive a sensed pressure from pressure sensor 42 via telemetry modules 30 and 88. Processor 84 estimates the pressure of reservoir 34 based on the pressure sensed by pressure sensor 42. Processor 84 determines a volume of fluid added to or removed from reservoir 34 based on the pressure sensed by pressure sensor 42 and the pressure of the reservoir estimated by processor 84. The volume of fluid added to or removed from reservoir 34 determined by processor 84 may be, e.g., stored in memory 86 of programmer 20 and/or transmitted to and stored in memory 28 of IMD 12. In some examples, processor 84 of programmer 20 may also combine the fluid volume added to or removed from reservoir 34 with a starting volume of therapeutic fluid in the reservoir to determine a fill status of the reservoir, e.g., to determine one of a total volume of therapeutic fluid in the reservoir, an indication that the reservoir is empty, an indication that the reservoir is being filled, or an indication that the reservoir is full. As described above, user interface 82 may display the fill status of reservoir 34 for viewing by a user including, e.g. patient 16 or a clinician.

Telemetry module 88 allows the transfer of data to and from IMD 12. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like.

Power source 90 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, reservoir pressure, volume and/or fill status, or any other information described herein to IMD 12. In this manner, the recharging device may be able to act as an intermediary communication device between external programmer 20 and IMD 12. Generally speaking, the techniques for determining a fill status of reservoir 34 described in this disclosure may be communicated to and from IMD 12 via any type of external device capable of electronic communications with the IMD.

Figure 4:
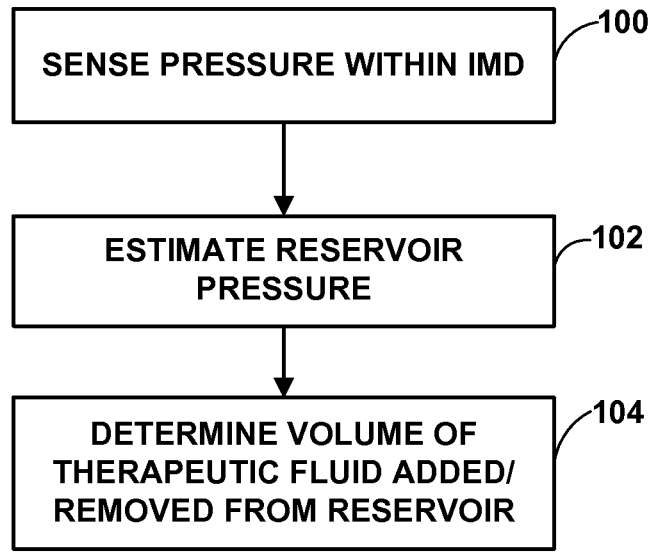
FIG. 4 is a flow diagram illustrating an example method of determining a fill status of a reservoir of an implantable fluid delivery device.

FIG. 4 is a flow diagram illustrating an example method, which may be employed, e.g., to determine a fill status of a reservoir of an IMD. The example method of FIG. 4 initially includes sensing a pressure within a fluid delivery device using a pressure sensor (100). The pressure within the reservoir of the fluid delivery device is estimated based on the sensed pressure (102). For example, the pressure may be adjusted downward for temperature drops in reservoir 34 or adjusted upward for rising temperatures in the reservoir according to a pressure temperature adjustment function. The volume of fluid added to or removed from the reservoir may be determined based on the sensed pressure and the estimated pressure of the reservoir (104).

The example method of FIG. 4 is described in greater detail below with reference to IMD 12 of FIGS. 1 and 2. However, methods in accordance with the techniques described in this disclosure may be equally applicable to other medical devices including, e.g., a fluid delivery device including multiple reservoirs and multiple pressure sensors. Additionally, although the functions associated with the method of FIG. 4 are generally described as executed by processor 26 of IMD 12 and supported by data stored in or retrieved from memory 28, in other examples, a processor and a memory of a different device, e.g. processor 84 and memory 86 of programmer 20, may be employed instead of or in conjunction with processor 26 and memory 28 to execute one or more of the described functions.

The method of FIG. 4 includes sensing a pressure within a fluid delivery device using a pressure sensor (100). As explained above with reference to FIG. 2, pressure sensor 42 may be arranged, generally speaking, to sense the pressure in refill port assembly 36 or reservoir 34 of IMD 12. The particular pressure within IMD 12 sensed by pressure sensor 42 and employed in the method of FIG. 4 will affect how the volume added to or removed from reservoir 34 will be determined.

In one example, sensing a pressure within a fluid delivery device using a pressure sensor (100) includes sensing a pressure in refill port assembly 36, e.g. chamber 48 of IMD 12 as the therapeutic fluid is added to or removed from reservoir 34. In such examples, the rate at which the therapeutic fluid is added to or removed from reservoir 34 may be calculated, from which the volume of fluid added or removed may be determined.

In practice, the rate at which therapeutic fluid is added to reservoir 34, e.g., via a hypodermic needle puncturing septum 46 of refill port assembly 36 of IMD 12 is generally unknown. However, the rate may be calculated by processor 26 based on the pressure in refill port assembly 36, the pressure in reservoir 34, and a known fluidic restriction between the refill port and reservoir. In particular, the rate, r, at which therapeutic fluid is added to or removed from reservoir 34 of IMD 12 is equal to the difference between the pressure in the refill port assembly 36 sensed by pressure sensor 42 and the pressure in the reservoir divided by a fluidic restriction constant for IMD 12. In other words, the rate, r, at which therapeutic fluid is added to or removed from reservoir 34 of IMD 12 may be determined according to the following formula, where $P_s$ is the pressure sensed by sensor 42, $P_R$ is the pressure of reservoir 34, and $R_{IMD}$ is the fluidic restriction constant.

$$r = \frac{P_s - P_R}{R_{IMD}}$$

The fluid restriction constant, $R_{IMD}$, is a constant for IMD 12 that generally represents resistance to fluid flow through the device, in this case from refill port assembly 36 to reservoir 34. The fluid restriction constant may be measured or calculated before IMD 12 is implanted within patient 16 and stored, e.g., in memory 28. The fluid restriction constant, $R_{IMD}$, may depend on, e.g., characteristics of valve 50 and the compliance of the fluid flow path between refill port assembly 36 and reservoir 34. In any event, in some examples, the rate, r, at which therapeutic fluid is added to reservoir 34 may be approximately equal to the difference between the pressure, Ps, in refill port assembly 36 sensed by pressure sensor 42 and the pressure, $P_R$, in reservoir 34 divided by the fluid restriction constant, $R_{IMD}$, of IMD 12.

In the above example in which pressure is sensed in refill port assembly 36 by pressure sensor 42, the pressure, $P_R$, of reservoir 34 is unknown. Therefore, in accordance with the method of FIG. 4, an estimate of the pressure, $P_{Re}$, of reservoir 34 is made based on the pressure, $P_s$, sensed by pressure sensor 42 (102). Estimating the pressure in reservoir 34 of IMD 12 may be complicated because the temperature, $T_R$, of the reservoir may vary as therapeutic fluid is added or removed.

Figure 5:
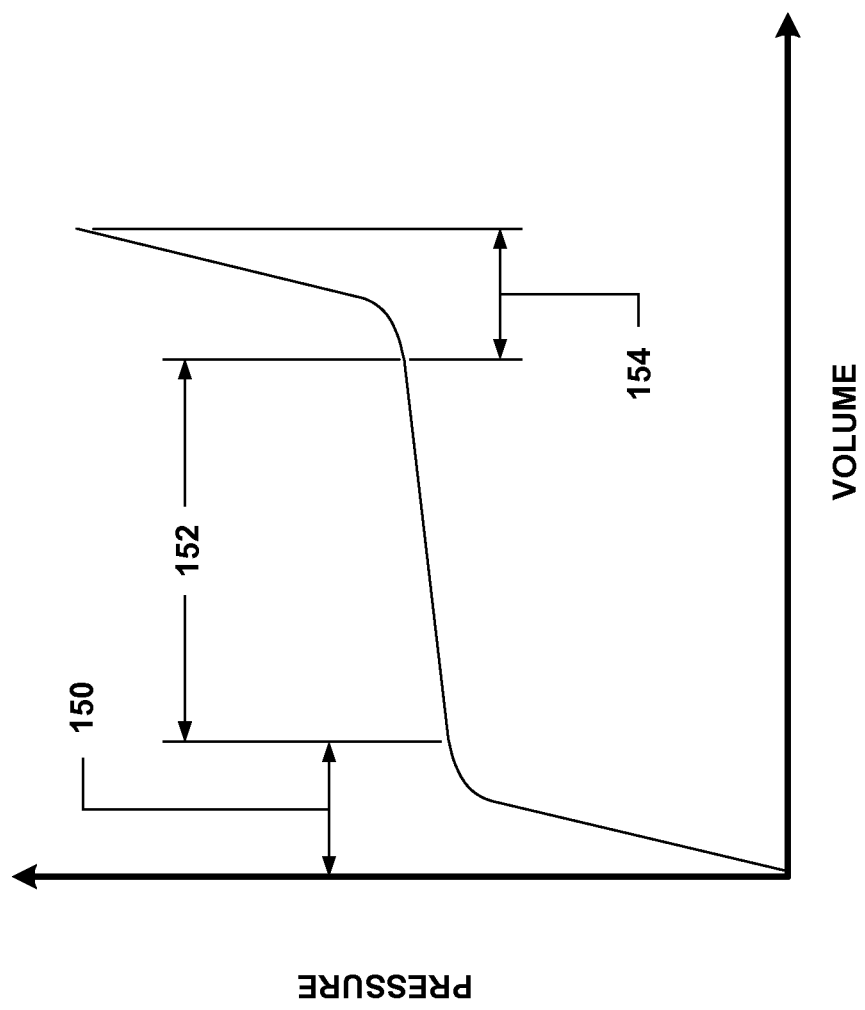
FIG. 5 is a graph illustrating an example constant reservoir temperature pressure-volume characteristic for an implantable fluid delivery device.

The equation for calculating the rate, r, at which therapeutic fluid is added to reservoir 34 set forth above assumes a constant temperature of reservoir 34, $T_R$, as the fluid is added or removed. In such examples, a constant temperature pressure-volume characteristic for IMD 12 during, e.g., a reservoir refill operation, may be determined. An example idealized pressure-volume characteristic of a reservoir of a fluid delivery device is illustrated in FIG. 5. The constant reservoir temperature pressure-volume characteristic generally includes three regions 150, 152, and 154. Region 150 is a non-linear region representing an initial period of time during which reservoir 34 transitions from an empty state to a filling state. Region 152 is a generally linear region during which reservoir 34 is continuously filled with therapeutic fluid, e.g., via a hypodermic needle puncturing septum 46 of refill port assembly 36. Region 154 is a non-linear region representing a final period during which reservoir 34 transitions from the filling state to a full state.

Figure 6:
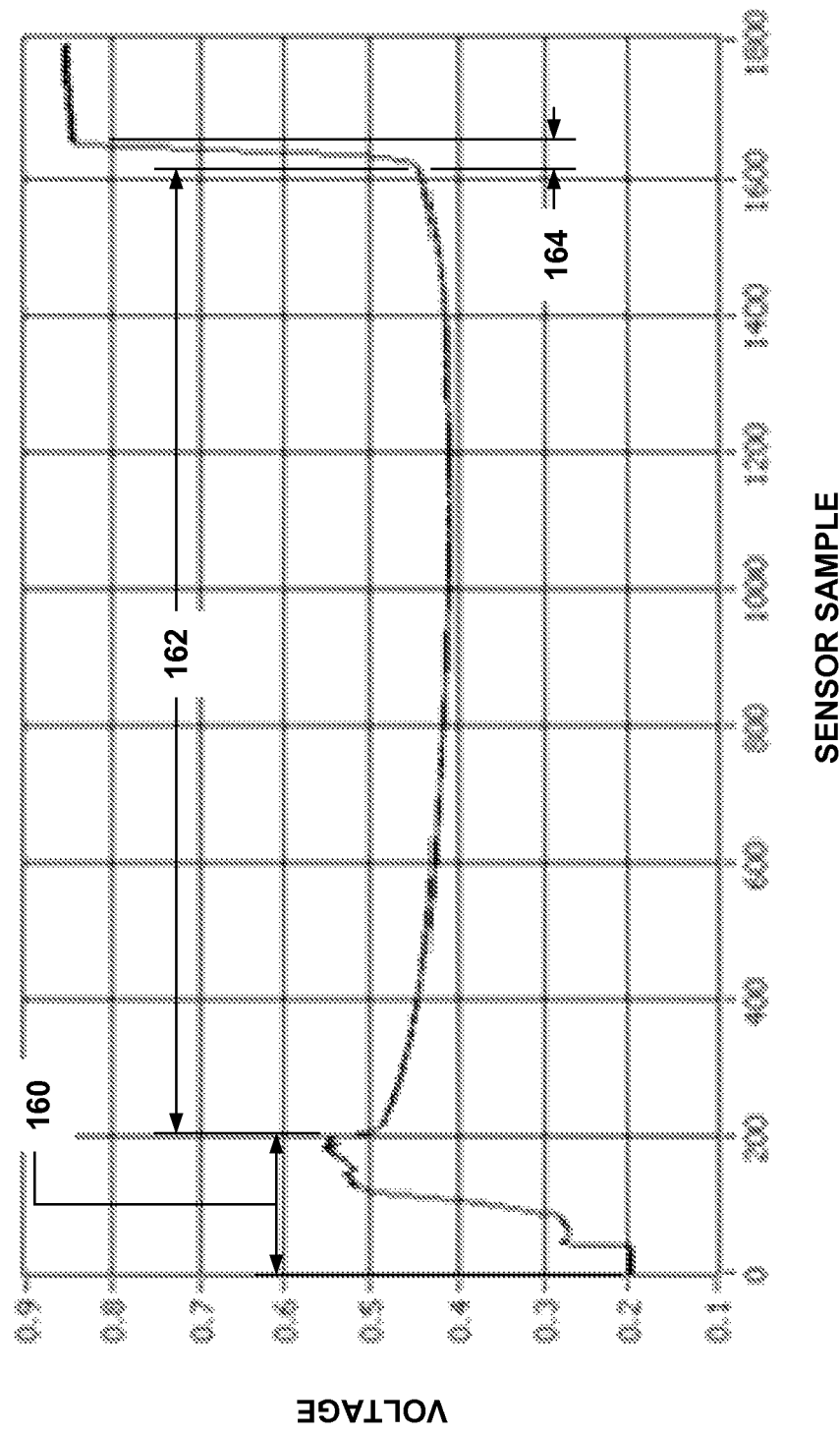
FIG. 6 is a graph illustrating voltage signals generated by a reservoir pressure sensor during a refill operation of a reservoir of a fluid delivery device.

In examples of filling reservoir 34 with a therapeutic fluid at a temperature that is not substantially equal to the initial temperature of the reservoir (which generally corresponds to the temperature of the body of patient 16), the temperature of the reservoir, $T_R$, may vary as the therapeutic fluid is added or removed. For example, while reservoir 34 may generally have an initial temperature approximately equal to the temperature of the body of patient 16, e.g., 35-37 degrees Celsius, the therapeutic fluid added to the reservoir of IMD 12 may have a temperature approximately equal to room temperature, e.g., 22 degrees Celsius. In examples in which the temperature of reservoir 34, $T_R$, is not constant, the pressure of the reservoir sensed using pressure sensor 42 (100) may be affected by the variations in temperature in the reservoir. For example, in contrast to the constant reservoir temperature pressure-volume characteristic illustrated in FIG. 5, FIG. 6 illustrates voltage signals generated by a pressure sensor during a refill operation of a reservoir of a fluid delivery device in which the temperature of the reservoir varies as the fluid is added. Changes in the voltage signals illustrated in FIG. 6 may generally correspond to, e.g., changes in the pressure of reservoir 34 of IMD 12 sensed by pressure sensor 42 either directly or indirectly across the fluidic restriction between the reservoir and refill port 36.

In FIG. 6, the variable reservoir temperature pressure-volume characteristic generally includes three regions 160, 162, and 164, which generally correspond to respective regions 150, 152, 154 of the constant reservoir temperature pressure-volume characteristic illustrated in FIG. 5. Region 160 represents an initial period of time during which reservoir 34 transitions from an empty state to a filling state. Region 162 represents a period of time during which reservoir 34 is continuously filled with therapeutic fluid, e.g., via a hypodermic needle puncturing septum 46 of refill port assembly 36. Region 164 represents a final period during which reservoir 34 transitions from the filling state to a full state. As illustrated in the example of FIG. 6, however, the pressure of reservoir 34 sensed by pressure sensor 42 actually drops for a portion of region 162 before eventually rising again before reaching the beginning of region 164.

The pressure drop in reservoir 34 during a period of increasing fluid volume illustrated in FIG. 6 is caused by the changes in temperature of the reservoir. In particular, the portion of region 162 during which the pressure of reservoir 34 sensed by pressure sensor 42 actually drops corresponds to a period of time during which the temperature effects on reservoir pressure overtake the volume effects. In other words, the reduction in the pressure of reservoir 34 caused by a cooler temperature therapeutic fluid being added to a warmer reservoir is greater than the pressure increase caused by the additional volume of fluid in the reservoir, which results in a net drop in the pressure in the reservoir. As fluid is added to reservoir 34, the effect of the added fluid volume on reservoir pressure eventually overtakes the reservoir temperature effects, which results in a net rise in the pressure in the reservoir as the pressure-volume characteristic illustrated in FIG. 6 approaches the transition from region 162 to region 164.

Referring again to the example method of FIG. 4, an estimate of the pressure, $P_{Re}$, of reservoir 34 is made based on the pressure, $P_s$, sensed by pressure sensor 42 (102). The estimated pressure, $P_{Re}$, in reservoir 34 with varying temperatures in the reservoir is a function of the accumulated volume of therapeutic fluid in the reservoir, $V_R$, the initial temperature of the reservoir, $T_{Ri}$, and the temperature of the therapeutic fluid, $T_F$. The estimated pressure of the reservoir, $P_{Re}$, can be calculated by processor 26 according to the following formula.

$$P_{Re} = K_t \left[ \left( \frac{(\beta \cdot T_{Ri}) + (\gamma \cdot T_f \cdot V)}{\beta + (\gamma \cdot V_R)} \right) - T_b \right] + P_A + (K_v \cdot V_R)$$

In the foregoing formula for calculating the estimated pressure of reservoir 34, $P_{Re}$, $K_t$ and $K_v$ are pressure sensitivity to temperature and volume changes, respectively. For example, $K_v$ is a characteristic of reservoir 34 of IMD 12 that behaves like a spring, e.g. in cases where the reservoir is formed as a resilient bellows, in which the spring constant or characteristic, $K_v$, represents the amount of incremental change in pressure in the reservoir per incremental change in volume of fluid in the reservoir. In other words, $K_v$ is approximately equal to $\Delta P_R / \Delta V_R$. $P_A$ is the pressure sensed by pressure sensor 42 at a particular inflection point (shown in FIG. 7) during a refill of IMD 12 and used to determine the initial temperature of the reservoir, $T_{Ri}$. $T_b$ is the temperature of the body of patient 16, which may be assumed to be approximately equal to the initial temperature of reservoir 34, $T_{Ri}$. $V_R$ is the approximate total volume in the reservoir accumulated during filling, and beta, $\beta$, and gamma, $\gamma$, are the heat capacities of IMD 12 and water, respectively.

The accumulated total volume in reservoir 34, $V_R$, may be stored on, e.g., memory 28 of IMD 12 by processor 26, as the device continuously monitors reservoir volume during, e.g., a refill operation. An initial or starting volume of therapeutic fluid in reservoir 34, e.g., at the point in time when the reservoir is initially filled with additional amounts of the fluid or another fluid, may be determined by processor 26 subtracting a volume of therapeutic fluid pumped from IMD 12 since a time at which the reservoir was last full from a volume of therapeutic fluid in the reservoir when the reservoir was last full, the values of which may be retrieved from, e.g., memory 28 by processor 26. In one example, the volume of therapeutic fluid pumped from IMD 12 may be determined by processor 26 multiplying a number of strokes of pump 32 by a volume of fluid pumped per stroke, each of which values may be stored in, e.g., memory 28.

In order to calculate the estimated pressure, $P_{Re}$, of reservoir 34 based on the formula set forth above, the initial temperature of the reservoir, $T_{Ri}$, e.g., during a refill operation of IMD 12, and the temperature of the therapeutic fluid, $T_F$ added to the reservoir must be known. In some examples, therefore, the initial temperature of the reservoir, $T_{Ri}$, and the temperature of the therapeutic fluid, $T_F$, added to the reservoir may be estimated by processor 26 based on the pressure sensed by pressure sensor 42.

Figure 7:
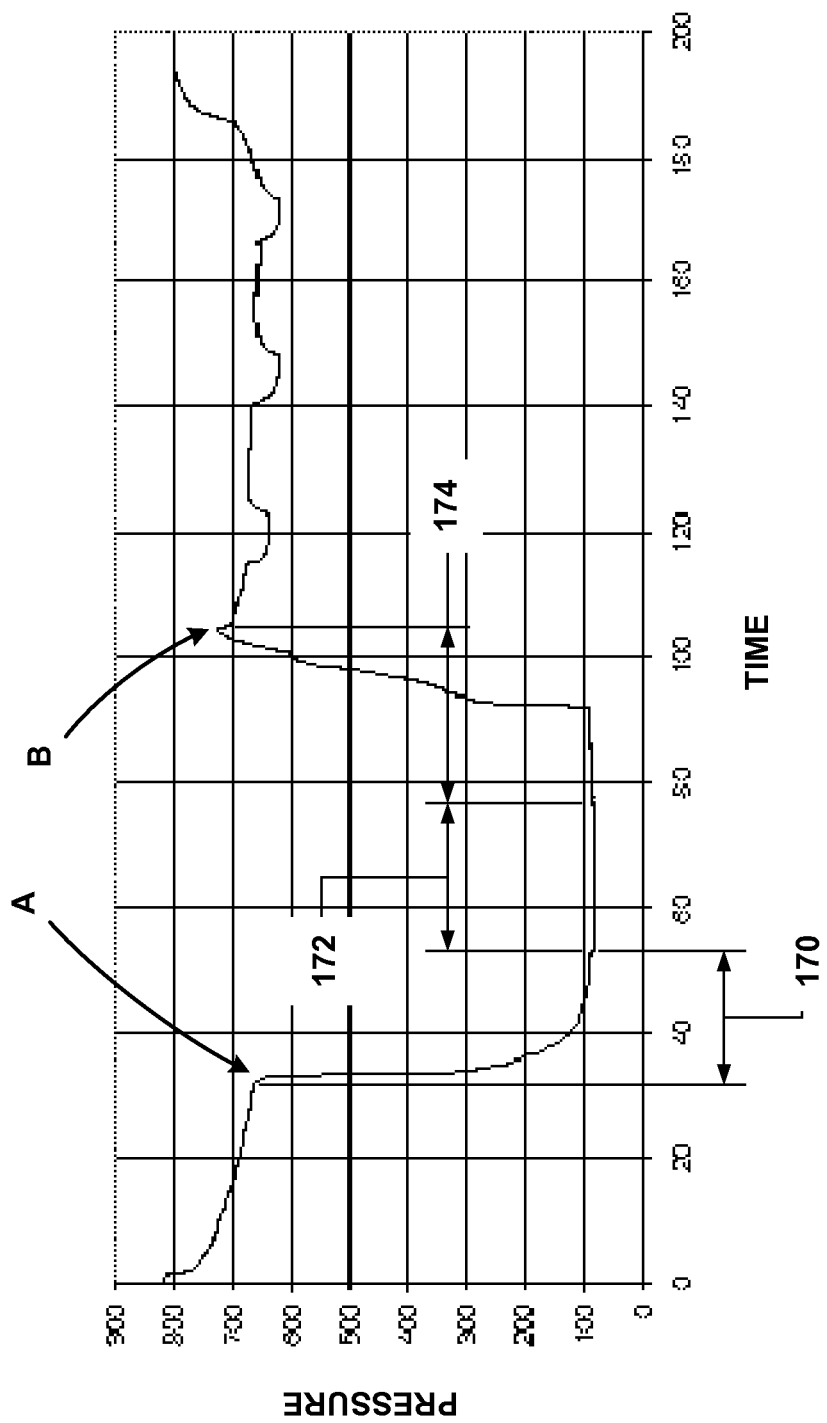
FIG. 7 is a graph illustrating reservoir pressure sensed by a pressure sensor over a period of time during a refill operation of a reservoir of a fluid delivery device.

Generally speaking, the initial temperature of reservoir 34, $T_{Ri}$, e.g., a refill operation of IMD 12, and the temperature of the therapeutic fluid, $T_F$, added to the reservoir may be estimated by identifying particular inflection points in the pressure profile sensed by pressure sensor 42 during, e.g., a refill operation. FIG. 7 illustrates the pressure in millimeters of Mercury (mmHg) in a reservoir of a fluid delivery device over a period of time in seconds of a refill operation of the device. The example of FIG. 7 may, e.g., be the pressure in refill port assembly 36 sensed by pressure sensor 42 and received and stored in memory 28 by processor 26 during a portion of a refill operation of the reservoir. The pressure profile of FIG. 7 is representative of the pressure of reservoir 34 of IMD 12, because the pressure in refill port assembly 36 sensed by pressure sensor 42 may differ by a relatively small amount from the reservoir pressure caused by the fluid restriction between refill port and reservoir. In the example of FIG. 7, the pressure profile sensed by pressure sensor 42 includes three regions 170, 172, and 174. Region 170 represents an initial period of time during which reservoir 34 transitions from being aspirated by a clinician to an empty state of the reservoir. Region 172 represents a period of time during which reservoir 34 is in the empty state. Region 174 represents a region during which reservoir 34 transitions from the empty state to a filling state.

The initial temperature of reservoir 34, $T_{Ri}$, may generally be described as the temperature of the reservoir at a pressure corresponding to the pressure at inflection A represented in the pressure profile illustrated in FIG. 7, which corresponds to a point at which the reservoir transitions between aspiration and an empty state. In some examples, inflection A may be identified by processor 26 based on signals from pressure sensor 42 by identifying the point at which a pressure differential, dP/dt, of the pressure sensed by pressure sensor 42 traverses a first threshold as the therapeutic fluid is removed from the reservoir during aspiration. Pressure differential, as used in this disclosure, generally refers to the first derivative of pressure with respect to time, or, that is, the rate of change of pressure with respect to time.

Figure 8:
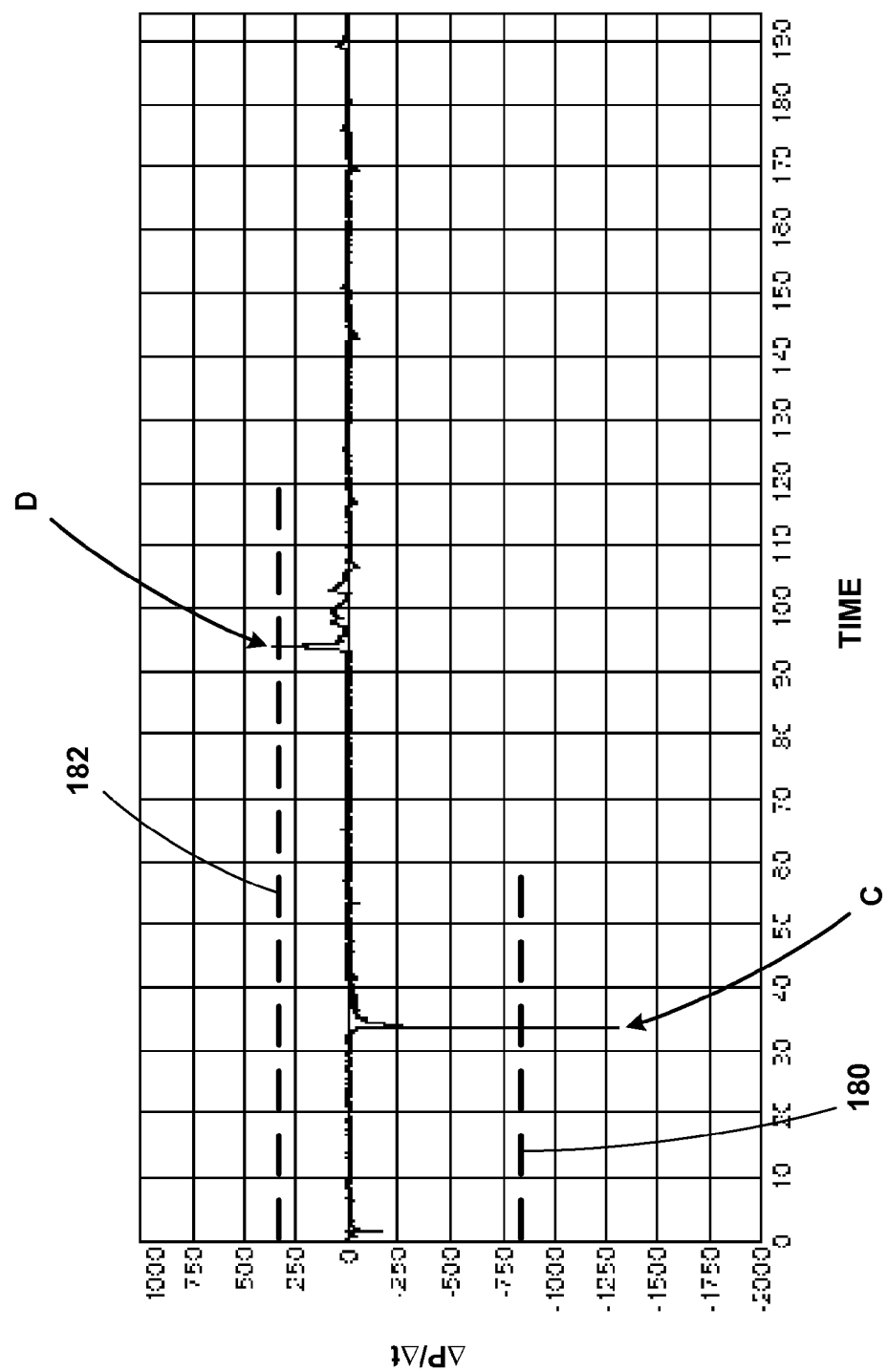
FIG. 8 is a graph illustrating the time rate of change of the sensed pressure shown in FIG. 7.

FIG. 8 illustrates an example of the time rate of change of the sensed pressure shown in FIG. 7. In practice, sensing pressure using pressure sensor 42 (100) includes sampling the pressure of, e.g. refill port assembly 36 at a number of times using pressure sensor 42, from which the pressure differential, dP/dt, may be numerically approximated by processor 26 as the change in pressure of the refill port from a first time to a second time, as illustrated in the following formula.

$$\frac{dP}{dt} \approx \frac{\Delta P}{\Delta t} = \frac{(P_i - P_{i-1})}{\Delta t}$$

In the process of sensing the pressure of refill port assembly 36 using pressure sensor 42 (100), therefore, a number of discrete pressure measurements of the pressure may be sensed at a number of times, the values of which may be stored, e.g., in memory 28 of IMD 12, and/or the memory of another device, e.g. memory 86 of programmer 20. For example, pressure sensor 42 may sense pressure $P_1$ of refill port assembly 36 at time $t_1$ and then sense pressure $P_2$ for the refill port at time $t_2$. In this example, the rate of change in pressure of refill port assembly 36 over a time period from time $t_1$ to time $t_2$ may be determined by processor 26 as equal to $(P_2-P_1)/\Delta t_{1 \to 2}$. Results of one example of this process for numerically estimating the pressure differential of refill port assembly 36 of IMD 12 is represented in FIG. 8 over a period of time corresponding to a portion of a refill operation of reservoir 34.

Processor 26 may monitor the pressure differential, $\Delta P/\Delta t$, determined based on the pressure sensed by pressure sensor 42, as therapeutic fluid is removed from reservoir 34, i.e., as the reservoir is aspirated and periodically compare the pressure differential values to a threshold value. In the event that processor 26 determines that the pressure differential, $\Delta P_R/\Delta t$, drops below a first threshold, the processor may store the sensed pressure in the reservoir as corresponding to inflection A in memory 28. For example, inflection A shown in FIG. 7 corresponds to the relatively large negative pressure differential spike C illustrated in FIG. 8, which drops below example threshold 180.

Figure 9:
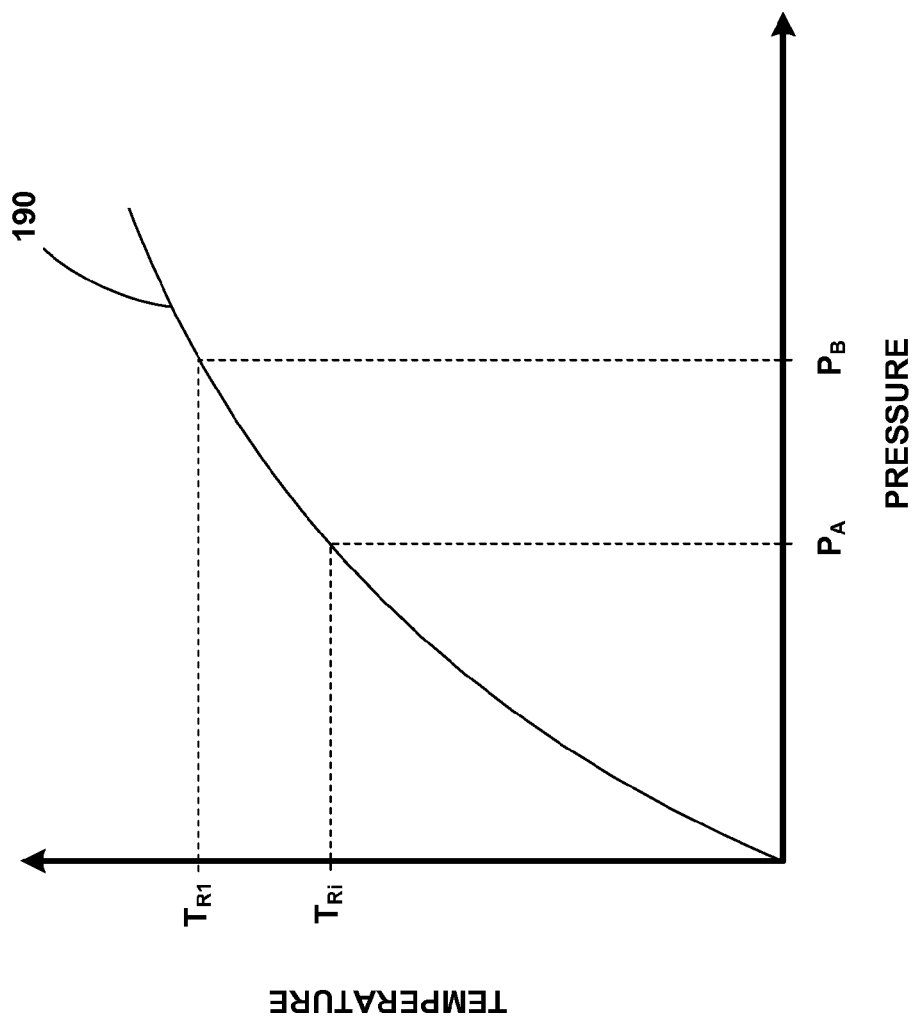
FIG. 9 is a graph illustrating an example temperature-pressure characteristic for an implantable fluid delivery device.

After the pressure in refill port assembly 36 at inflection A, $P_A$, shown in FIG. 7 has been identified and stored in memory 28 by processor 26, the processor may determine an estimate of the initial temperature of reservoir 34, $T_{Ri}$, by correlating the pressure at inflection A, $P_A$, to a temperature on a known temperature-pressure characteristic for IMD 12. An example temperature-pressure characteristic is illustrated in FIG. 9. In the example of FIG. 9, curve 190 is a temperature-pressure curve known for a particular gas propellant used to pressurize reservoir 34 in IMD 12. For each temperature value on curve 190 of FIG. 9, there is a corresponding pressure-volume characteristic in accordance with the example shown in FIG. 5. The particular pressure-volume characteristic corresponding to the temperature on curve 190 of FIG. 9 will simply move up or down along the pressure ordinate axis depending on the magnitude of the temperature. The known temperature-pressure characteristic for the propellant gas that pressurizes reservoir 34 may be employed in the calculation of the initial temperature of reservoir 34, $T_{Ri}$, as the temperature of the reservoir generally does not vary during aspiration of IMD 12. It is noted that the temperature of reservoir 34 of IMD 12 and the temperature of the gas propellant that pressurizes the reservoir are generally assumed to be approximately equal in the example techniques described for determining the fill status of the reservoir. As such, curve 190 may generally be assumed to correspond to a temperature-pressure curve known for reservoir 34 of IMD 12.

In one example, the temperature-pressure characteristic for IMD 12, e.g. the example illustrated in FIG. 9, may be employed to develop a look-up table stored in memory 28, from which processor 26 may look-up a temperature corresponding to the pressure at inflection A, $P_A$, to determine the initial temperature of reservoir 34, $T_{Ri}$. The look-up table may store a set of temperatures that are indexed to particular pressure values. By indexing the pressure at inflection A to a corresponding temperature in the look-up table, the temperature can be determined. In another example, the temperature-pressure characteristic for IMD 12 may be employed to develop an interpolation function stored in memory 28, from which processor 26 may calculate the initial temperature of reservoir 34, $T_{Ri}$, as a function of the pressure, $P_A$, at inflection A.

In order to estimate the pressure, $P_{Re}$, of reservoir 34 based on the pressure, $P_s$, sensed by pressure sensor 42 (102), the temperature of the therapeutic fluid, $T_F$, in addition to the initial temperature of the reservoir, $T_{Ri}$, may be estimated by processor 26 based on the sensed pressure. The temperature of the therapeutic fluid, $T_F$, added to reservoir 34 may generally be described as a function of the initial temperature of the reservoir, $T_{Ri}$, and the temperature of the reservoir at inflection point B, $T_{R1}$, represented in the pressure profile illustrated in FIG. 7, which corresponds to a transition between an empty state and a filling state of the reservoir. The initial temperature of the reservoir, $T_{Ri}$, may be estimated as described above with reference to FIGS. 7-9. In order to determine the temperature of reservoir 34 at inflection point B, $T_{R1}$, in some examples, inflection B may be identified by processor 26 based on signals from pressure sensor 42 by identifying a local maximum pressure sensed by pressure sensor 42 as the therapeutic fluid is added to the reservoir during filling by a clinician after aspiration.

Identifying the local maximum pressure that corresponds to inflection B of FIG. 7 and thereby signals a transition between an empty state and a filling state of reservoir 34 may be accomplished in a number of ways. For example, processor 26 may determine that a first derivative of the pressure sensed by pressure sensor 42 with respect to time, ΔP/Δt, traverses a second threshold as the therapeutic fluid is added to the reservoir. In one example, processor 26 may monitor the pressure differential as therapeutic fluid is added to the reservoir and periodically compare the values to a threshold value. In the event that processor 26 determines that the pressure differential of the pressure sensed by pressure sensor 42 rises above a second threshold, the processor 26 may store the pressure sensed by pressure sensor 42 at this time as corresponding to inflection B in memory 28. For example, in FIG. 8, inflection B shown in FIG. 7 corresponds to the relatively large positive pressure differential spike D illustrated in FIG. 8, which rises above example threshold 182.

In another example, the local maximum pressure that corresponds to inflection B of FIG. 7 may be identified by processor 26 determining that a difference between a first pressure sensed by pressure sensor 42 at a first time and a second pressure sensed by the pressure sensor at a second time traverses a third threshold. The third threshold may be represented as an absolute value or a percentage of the higher first pressure at the first time.

In another example, the local maximum pressure that corresponds to inflection B of FIG. 7 may be identified by processor 26 determining an amount of time since a change in a local maximum pressure sensed using pressure sensor 42 has traversed a fourth threshold. In other words, for example, processor 26 may monitor the pressure of refill port assembly 36 sensed by pressure sensor 42 and the time over which it is measured. In the event that a possible maximum pressure value sensed by pressure sensor 42 remains greater than subsequent pressure values for a period of time greater than a threshold time, processor 26 may store the possible maximum pressure value as the local maximum pressure corresponding to inflection B in memory 28.

After the pressure, $P_B$, sensed by pressure sensor 42 at inflection B, shown in FIG. 7, has been identified and stored in memory 28 by processor 26, the processor may determine an estimate of the temperature, $T_{R1}$, of the reservoir at inflection point B by correlating the pressure, $P_B$, at inflection B to a temperature on a known temperature-pressure characteristic for IMD 12. For example, processor 26 may determine the temperature, $T_{R1}$, of the reservoir at inflection point B based on the temperature-pressure characteristic illustrated in FIG. 9. As described above with reference to the estimation of the initial temperature of reservoir 34, $T_{Ri}$, in the example of FIG. 9, curve 190 is a temperature-pressure curve known for a particular gas propellant used to pressurize reservoir 34 in IMD 12. The known temperature-pressure characteristic for the propellant gas that pressurizes reservoir 34 may be employed in the calculation of the initial temperature of reservoir 34, $T_{Ri}$, as variations in the temperature of the reservoir are negligible during the initial phase of filling the reservoir with a therapeutic fluid.

In one example, the temperature-pressure characteristic for IMD 12, e.g., the example illustrated in FIG. 9, may be employed to develop a look-up table stored in memory 28, from which processor 26 may look-up the temperature corresponding to the pressure at inflection B, $P_B$, to determine the temperature of the reservoir at inflection point B, $T_{R1}$. In another example, the temperature-pressure characteristic for IMD 12 may be employed to develop an interpolation function stored in memory 28, from which processor 26 may calculate the temperature of the reservoir at inflection point B, $T_{R1}$, as a function of the pressure at inflection B, $P_B$.

After the initial temperature of reservoir 34, $T_{Ri}$, and the temperature of the reservoir at inflection point B, $T_{R1}$, have been determined as set forth above, processor 26 may calculate the temperature of the therapeutic fluid, $T_F$, added to the reservoir as a function of the two temperatures according to the following formula.

$$T_F \frac{\beta}{\gamma} \cdot \frac{1}{V_R} \cdot (T_{R1} - T_{Ri}) + T_{R1}$$

In the formula set forth above for calculating the temperature of the therapeutic fluid, $T_F$, added to reservoir 34 as a function of the initial temperature of reservoir 34, $T_{Ri}$, and the temperature of the reservoir at inflection point B, $T_{R1}$, $V_R$ is the approximate total volume in the reservoir accumulated during filling, and beta, β, and gamma, γ, are the heat capacities of IMD 12 and water, respectively. The accumulated total volume in reservoir 34, $V_R$, may be stored on, e.g., memory 28 of IMD 12 by processor 26, as the device continuously monitors reservoir volume during, e.g., a refill operation. An initial or starting volume of therapeutic fluid in reservoir 34, e.g., at the point in time when the reservoir is initially filled with additional amounts of the fluid or another fluid, may be determined by processor 26 subtracting a volume of therapeutic fluid pumped from IMD 12 since a time at which the reservoir was last full from a volume of therapeutic fluid in the reservoir when the reservoir was last full, the values of which may be retrieved from, e.g., memory 28 by processor 26. In one example, the volume of therapeutic fluid pumped from IMD 12 may be determined by processor 26 multiplying a number of strokes of pump 32 by a volume of fluid pumped per stroke, each of which values may be stored in, e.g., memory 28.

In some examples in which the initial temperature of reservoir 34, $T_{Ri}$, and the temperature of the therapeutic fluid, $T_F$, are estimated by processor 26 based on the pressure in refill port assembly 36 sensed by pressure sensor 42 at inflections A and B, respectively, in FIG. 7, the sensed pressure at each inflection point may be adjusted for fluidic restriction in IMD 12 by adding the fluid restriction constant, $R_{IMD}$, to each sensed pressure value. The pressure value adjusted for fluidic restriction may then be correlated to a temperature in a known temperature-pressure characteristic for IMD 12 including, e.g., the example temperature-pressure characteristic illustrated in FIG. 9. Therefore, instead of assuming that the error between the pressure in refill port assembly 36 sensed by pressure sensor 42 and the pressure in reservoir 34 is negligible, the sensed pressure may be adjusted by the known fluid restriction constant, RIMD, to more closely reflect the pressure in the reservoir.

Referring again to FIG. 4, the example method includes, in addition to estimating reservoir pressure (102), determining the volume of fluid added to or removed from reservoir 34 based on the pressure sensed by pressure sensor 42 and the estimated pressure of the reservoir (104). In some examples, employing the initial temperature of reservoir 34, $T_{Ri}$, and the temperature of the therapeutic fluid, $T_F$, estimated by processor 26 based on the pressure sensed by pressure sensor 42, the processor may estimate the pressure of the reservoir, $P_{Re}$, (102) according to the formula set forth above. Once processor 26 calculates the estimated pressure of reservoir 34, $P_{Re}$, the rate at which the therapeutic fluid is added to or removed from the reservoir, r, may be determined, according to the following formula, where $P_s$ is the pressure sensed by sensor 42, $P_{Re}$ is the estimated pressure of the reservoir, and $R_{IMD}$ is the fluidic restriction constant.

$$r = \frac{P_s - P_{Re}}{R_{IMD}}$$

In such examples, the volume of therapeutic fluid added to or removed from reservoir 34, $\Delta V_R$, of IMD 12 may generally be calculated by processor 26 by integrating the volumetric rate, r, at which therapeutic fluid is added or removed from the reservoir over time, t, according to the following formula.

$$\Delta V_R = \int_{start}^{end} r\, dt$$

In practice, the volume of fluid added to or removed from reservoir 34, $\Delta V_R$, may be determined (104) by processor 26 executing the numerical equivalent of integrating the calculated rate at which therapeutic fluid is added to the reservoir, r, over a time during which pressure is sensed by pressure sensor 42 in accordance with the following formula.

$$\Delta V_R = \sum_{start}^{end} r\Delta t$$

In some examples, the total volume of therapeutic fluid accumulated in reservoir 34, $V_R$, may be calculated by adding the existing volume of fluid in the reservoir to the volume of fluid added to or removed from reservoir 34, $\Delta V_R$. As noted above, an initial or starting volume of therapeutic fluid in reservoir 34, e.g., at the point in time when the reservoir is initially filled with additional amounts of the fluid or another fluid, may be determined by processor 26 subtracting a volume of therapeutic fluid pumped from IMD 12 since a time at which the reservoir was last full from a volume of therapeutic fluid in the reservoir when the reservoir was last full.

In addition to calculating the total volume of therapeutic fluid accumulated in reservoir 34, processor 26 may cause the fill status, e.g. the total volume of fluid in the reservoir or the fill state as empty, filling, or full, to be displayed by an external display device, e.g. user interface 82 of programmer 20. In some examples, the total accumulated volume of fluid in reservoir 34 and the fill state as, e.g., empty, filling, or full may be caused to be displayed by processor 26. For example, as described above with reference to FIGS. 2 and 3, processor 26 may be configured to prompt user interface 82 of programmer 20 to present a user with an indicator of fluid addition or removal upon determining that the pressure sensed by pressure sensor 42 is indicative of fluid being withdrawn from or added to reservoir 34. In addition, the pressure sensed by the pressure sensor 42 may be interpreted by processor 26 as indicating that reservoir 34 is empty, filling, or full, in which case the processor may prompt user interface 82 to display an indication of empty, filling, or full to the user. In other examples, the information from pressure sensor 42 may be employed to calculate the volume of therapeutic fluid in reservoir 34, which, in turn may be displayed by user interface 82 of programmer 20, or another external display device. Example graphical displays of the fill status of a reservoir of an IMD similar to the reservoir 34 of IMD 12 described in this disclosure are provided in related U.S. patent application Ser. No. 12/619,145, entitled "PRESSURE BASED REFILL STATUS MONITOR FOR IMPLANTABLE PUMPS," filed Nov. 16, 2009.

In some examples, processor 26 may also trigger one or more alarms based on the information transmitted by pressure sensor 42 including, e.g., an empty, filling, or full reservoir alarm. Alarms triggered by processor 26, or another component of IMD 12 or another device, e.g. programmer 20, may generally include audible, tactile, and/or visual alerts. For example, a reservoir empty, filling, or full state alarm may include audible alerts issued by programmer 20 or another external device associated with therapy system 10 (see FIG. 1). In another example, a reservoir fill status alarm includes processor 26 causing IMD 12 to vibrate within the body of patient 16, thereby providing a tactile alert. In other examples, the alarm includes text or graphical messages delivered to patient 16 and/or a clinician via text message or e-mail displayed by programmer 20 or another electronic device communicatively connected to IMD 12 and/or programmer 20, thereby providing a visual alert.

As noted above, the foregoing example of executing the method of FIG. 4 assumes that sensing a pressure within a fluid delivery device (100) includes sensing a pressure in refill port assembly 36, e.g. chamber 48 of IMD 12. In another example of the method of FIG. 4, however, sensing a pressure within a fluid delivery device (100) includes sensing a pressure of reservoir 34 with pressure sensor 42 as the therapeutic fluid is added to or removed from the reservoir. For example, pressure sensor 42 may be located not in chamber 48 of refill port assembly 36, but, instead, in reservoir 34 to measure the pressure of the reservoir directly.

In such reservoir pressure sensing examples, similar to the previously explained refill port pressure sensing example, the pressure of reservoir 34 in circumstances including temperature variations in the reservoir will be estimated based on the pressure of the reservoir sensed by pressure sensor 42 (102). The estimate of the pressure, $P_{Re}$, of reservoir 34 based on the sensed pressure, $P_S$, of the reservoir (102) reflects a prediction of the future reservoir pressure based on the previous sensed pressure that is predicated on pressure-temperature characteristics of IMD 12. As such, the difference between the estimated pressure, $P_{Re}$, of reservoir 34 and the sensed pressure, $P_S$, of the reservoir represents a change in pressure, $\Delta P_R$, of the reservoir over time.

The estimated pressure, $P_{Re}$, of reservoir 34 may be calculated in the same manner as explained above as a function of the initial temperature of the reservoir, $T_{Ri}$, e.g., during a refill operation of IMD 12, and the temperature of the therapeutic fluid, $T_F$, added to the reservoir. The initial temperature of the reservoir, $T_{Ri}$, and the temperature of the therapeutic fluid, $T_F$, added to the reservoir may be estimated by processor 26 based on the pressure sensed by pressure sensor 42. In particular, the initial temperature of reservoir 34, $T_{Ri}$, and the temperature of the therapeutic fluid, $T_F$, are estimated by processor 26 based on the pressure in reservoir 34 sensed by pressure sensor 42 at inflections A and B, respectively, in FIG. 7. However, in reservoir pressure sensing examples of the method of FIG. 4, the pressure of reservoir 34 sensed by pressure sensor 42 at inflections A and B need not be adjusted for fluidic restriction in IMD 12 by adding the fluid restriction constant, $R_{IMD}$, to each sensed pressure value, because the pressure of the reservoir is being measured directly instead of calculated based on the sensed pressure in refill port assembly 36 and a known fluidic restriction constant of IMD 12, as described above in the refill port pressure sensing example of the method of FIG. 4.

Unlike the foregoing refill port pressure sensing example, the rate, r, at which the therapeutic fluid is added to or removed from reservoir 34 may not be calculated in reservoir pressure sensing examples of the method of FIG. 4, because the difference in pressure between refill port assembly 36 and the reservoir cannot be determined when pressure sensor 42 is arranged to measure the pressure in the reservoir directly. Instead of employing the therapeutic fluid rate to determine the volume of fluid added or removed (104), therefore, reservoir pressure sensing examples of the method of FIG. 4 employ a known relationship between incremental changes in pressure and incremental changes in volume in reservoir 34 to determine the volume of therapeutic fluid added to or removed from the reservoir (104).

As explained above, reservoir 34 of IMD 12 may have a known pressure sensitivity to volume changes characteristic, $K_v$, that behaves like a spring, e.g. in cases where the reservoir is formed as a resilient bellows. In particular, the spring constant or characteristic, $K_v$, represents the amount of incremental change in pressure in the reservoir per incremental change in volume of fluid in the reservoir. In other words, $K_v$ is approximately equal to $\Delta P_R/\Delta V_R$. As explained above, the estimated pressure, $P_{Re}$, of reservoir 34 reflects a prediction of the future reservoir pressure based on the previously sensed pressure, $P_S$, the difference between which, $P_S-P_{Re}$, therefore, represents a change in pressure, $\Delta P_R$, of the reservoir over time. Therefore, in examples of the method of FIG. 4 in which sensing a pressure within a fluid delivery device (100) includes sensing a pressure of reservoir 34 with pressure sensor 42 as the therapeutic fluid is added to or removed from the reservoir, the volume, $\Delta V_R$, of fluid added or removed from the reservoir may be determined according to the following formula.

$$\Delta V_R = \frac{P_s - P_{Re}}{K_V}$$

As with the refill port pressure sensing example, in some reservoir pressure sensing examples of the method of FIG. 4, the total volume of therapeutic fluid accumulated in reservoir 34, $V_R$, may be calculated by adding the existing volume of fluid in the reservoir to the volume of fluid added to or removed from reservoir 34, $\Delta V_R$. As noted above, an initial or starting volume of therapeutic fluid in reservoir 34, e.g., at the point in time when the reservoir is initially filled with additional amounts of the fluid or another fluid, may be determined by processor 26 subtracting a volume of therapeutic fluid pumped from IMD 12 since a time at which the reservoir was last full from a volume of therapeutic fluid in the reservoir when the reservoir was last full.

Figure 10:
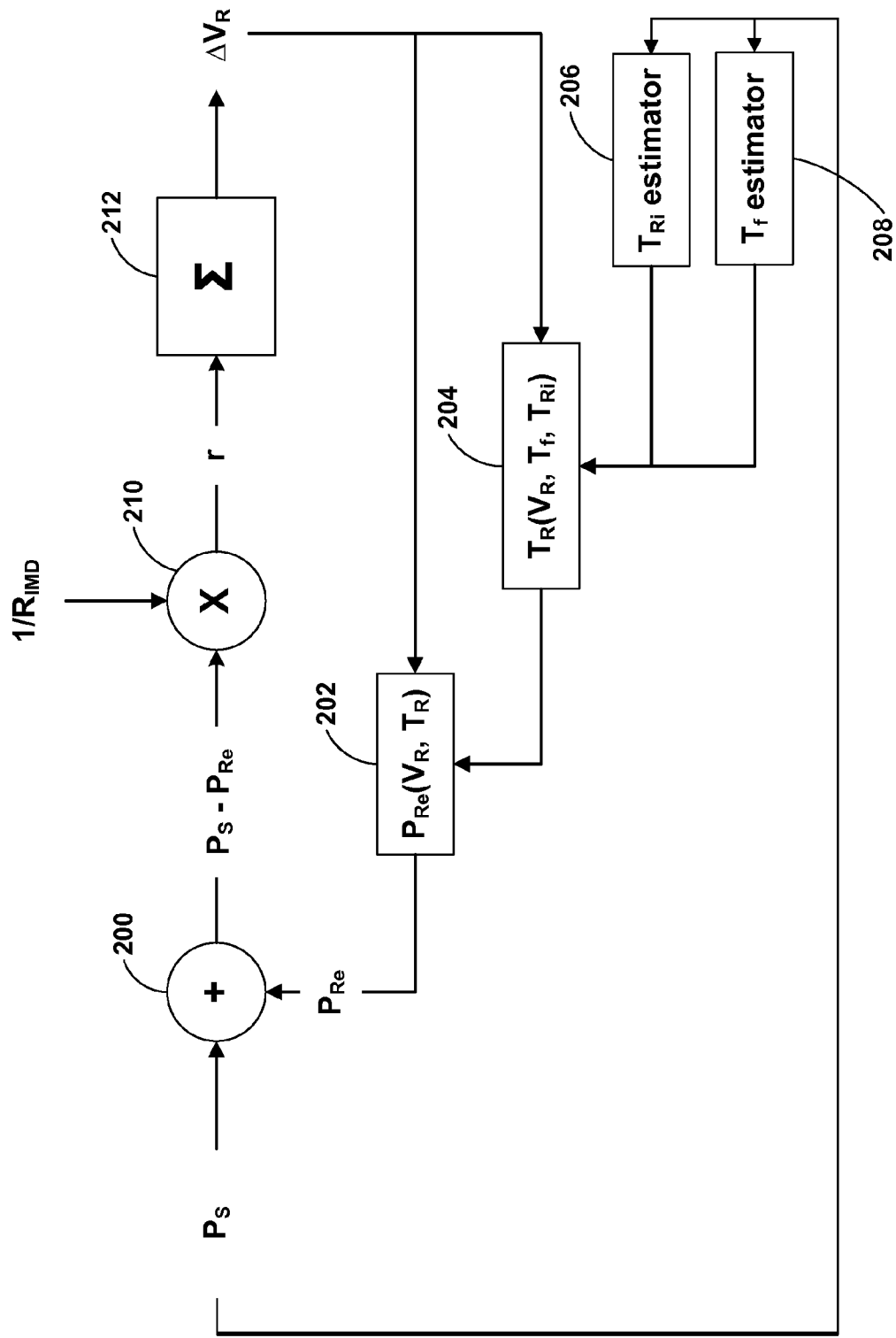
FIG. 10 is a diagram illustrating an example algorithm for determining a fill status of a reservoir of an implantable fluid delivery device.

An algorithm executed by, e.g., processor 26 of IMD 12 to implement functions for determining the fill status and/or volume of reservoir 34 in accordance with the refill port pressure sensing example of the method of FIG. 4 is illustrated in the diagram of FIG. 10. In FIG. 10, the example algorithm has as an input pressure, $P_S$, of reservoir 34 sensed by pressure sensor 42 and has as an output a volume, $\Delta V_R$, of therapeutic fluid added to or removed from the reservoir.

The estimated pressure, $P_{Re}$, of reservoir 34 is calculated as a function of the volume, $V_R$, of therapeutic fluid accumulated in the reservoir and an estimate of the temperature, $T_R$, of the reservoir at function block 202. The volume, $V_R$, of fluid accumulated in reservoir 34 may be known based on previous determinations of the volume, $\Delta V_R$, of fluid added or removed and/or a known or calculated starting volume of fluid in the reservoir. The estimated temperature, $T_R$, of reservoir 34 may be calculated by processor 26 at function block 204 as a function of the volume, $V_R$, of therapeutic fluid accumulated in the reservoir, a temperature, $T_f$, of the therapeutic fluid added to or removed from the reservoir, and an initial temperature, $T_{Ri}$, of the reservoir as the therapeutic fluid is added or removed. As described above with reference to the refill port pressure sensing example of the method of FIG. 4, processor 26 may estimate both the temperature, $T_f$, of the therapeutic fluid added to or removed from reservoir 34, and the initial temperature, $T_{Ri}$, of the reservoir as the therapeutic fluid is added or removed based on the pressure, $P_S$, of the reservoir sensed by pressure sensor 42 at function blocks 206 and 208, respectively.

After the estimated pressure, $P_{Re}$, of reservoir 34 is calculated by processor 26 and subtracted from the pressure, $P_S$, of the reservoir sensed by pressure sensor 42 at summing block 200, processor 26 may divide the difference by a fluid restriction constant, $R_{IMD}$, for IMD 12 at product block 210 to determine the volumetric rate, r, at which the therapeutic fluid is added to or removed from the reservoir. Processor 26 may then sum the rate, r, at which the therapeutic fluid is added to or removed from reservoir 34 over a time, $\Delta t$, during which the fluid is added or removed at integral block 212 to determine the volume, $\Delta V_R$, of therapeutic fluid added to or removed from the reservoir.

Figure 11:
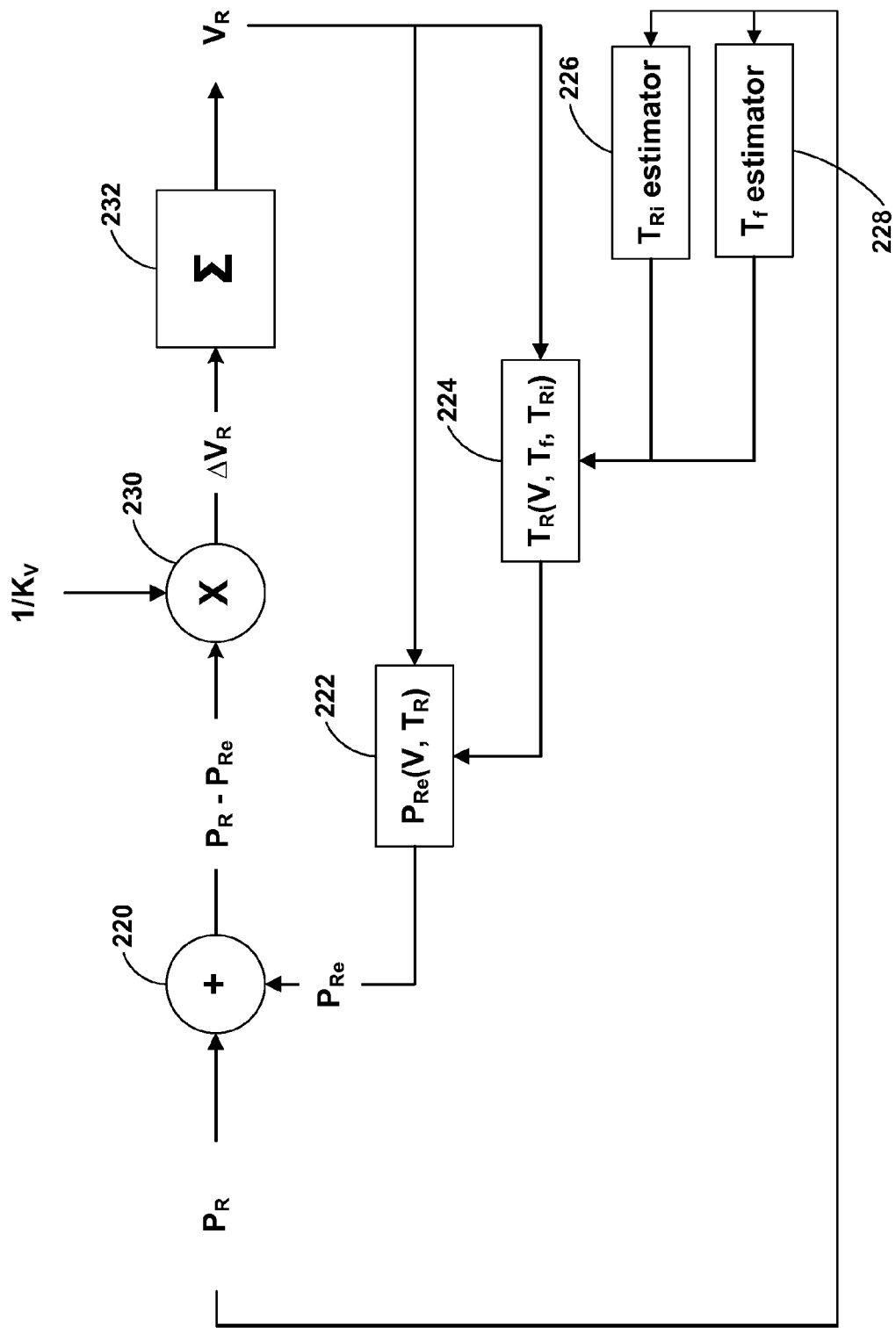
FIG. 11 is a diagram illustrating another example algorithm for determining a fill status of a reservoir of an implantable fluid delivery device.

An algorithm executed by, e.g., processor 26 of IMD 12 to implement functions for determining the fill status and/or volume of reservoir 34 in accordance with the reservoir pressure sensing example of the method of FIG. 4 is illustrated in the diagram of FIG. 11. In FIG. 11, the example algorithm has as an input pressure, $P_S$, of reservoir 34 sensed by pressure sensor 42 and has as an output a volume, $\Delta V_R$, of therapeutic fluid added to or removed from the reservoir.

The estimated pressure, $P_{Re}$, of reservoir 34 is calculated as a function of the volume, $V_R$, of therapeutic fluid accumulated in the reservoir and an estimate of the temperature, $T_R$, of the reservoir at function block 222. The volume, $V_R$, of fluid accumulated in reservoir 34 may be known based on previous determinations of the volume, $\Delta V_R$, of fluid added or removed and/or a known or calculated starting volume of fluid in the reservoir. The estimated temperature, $T_R$, of reservoir 34 may be calculated by processor 26 at function block 224 as a function of the volume, $V_R$, of therapeutic fluid accumulated in the reservoir, a temperature, $T_f$, of the therapeutic fluid added to or removed from the reservoir, and an initial temperature, $T_{Ri}$, of the reservoir as the therapeutic fluid is added or removed. As described above, processor 26 may estimate both the temperature, $T_f$, of the therapeutic fluid added to or removed from reservoir 34, and the initial temperature, $T_{Ri}$, of the reservoir as the therapeutic fluid is added or removed based on the pressure, $P_S$, of the reservoir sensed by pressure sensor 42 at function blocks 226 and 228, respectively.

After the estimated pressure, $P_{Re}$, of reservoir 34 is calculated by processor 26 and subtracted from the pressure, $P_S$, of the reservoir sensed by pressure sensor 42 at summing block 220, processor 26 may divide the difference by a known pressure sensitivity to volume changes characteristic, KV, for the reservoir of IMD 12 at product block 230 to determine the volume, $\Delta V_R$, of therapeutic fluid added to or removed from the reservoir. The total volume of therapeutic fluid accumulated in reservoir 34, $V_R$, may be calculated at summing block 232 by adding the existing volume of fluid in the reservoir, e.g. the starting volume or the volume calculated in previous iterations of the algorithm of FIG. 11, to the volume of fluid added to or removed from reservoir 34, $\Delta V_R$.

Figure 12:
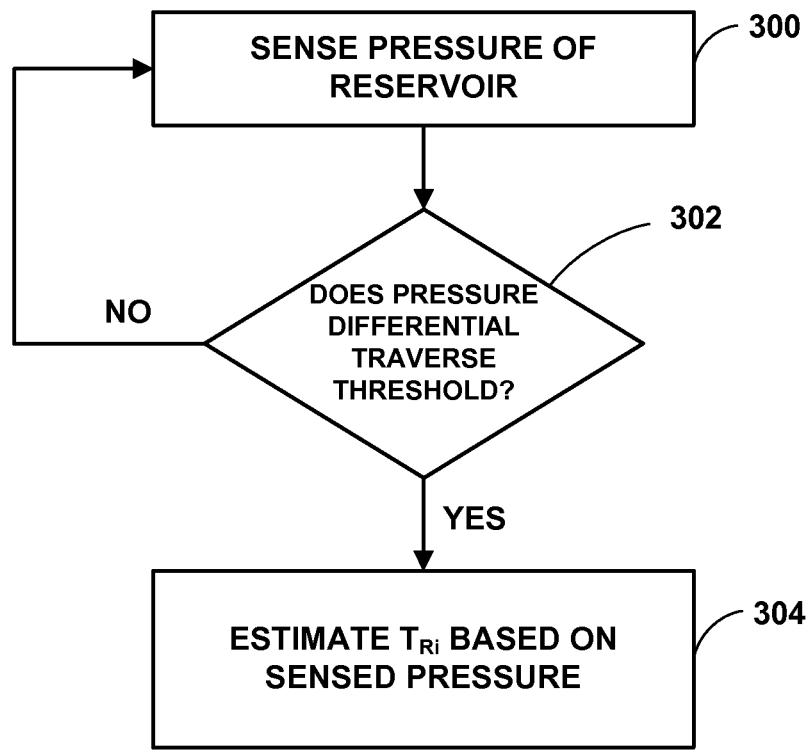
FIG. 12 is a flow diagram illustrating an example method of estimating a temperature of a reservoir of an implantable fluid delivery device.
Figure 13:
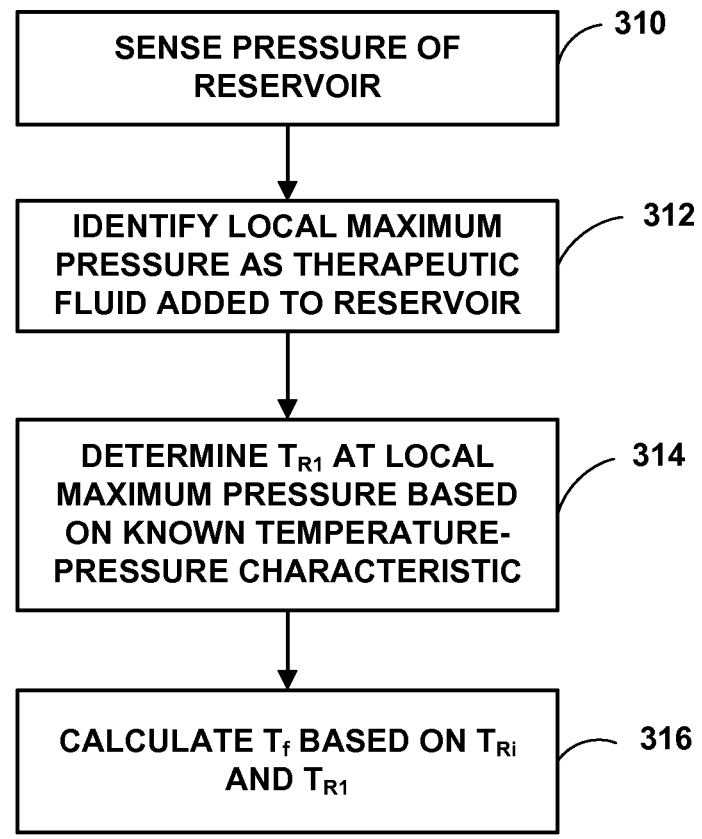
FIG. 13 is a flow diagram illustrating an example method of estimating a temperature of the therapeutic fluid added to a reservoir of an implantable fluid delivery device.

In some circumstances, it may be useful to estimate the initial temperature of reservoir 34, $T_{Ri}$, as a therapeutic fluid is removed from the reservoir, e.g., during aspiration of IMD 12, and the temperature of the fluid, $T_F$, as it is added to the reservoir after aspiration independent of any determination of the fill status of the reservoir. For example, clinicians may prescribe short duration infusion boluses for which the actual delivered dose is subject to the pressure of reservoir 34 of IMD 12, which is, in turn, subject to temperature changes over time. In such examples, the initial temperature of reservoir 34, $T_{Ri}$, and the temperature of the therapeutic fluid, $T_F$, may be used, e.g., to calculate a volume correction factor resulting in a more accurate delivery system. Therefore, FIGS. 12 and 13 show flow diagrams illustrating example methods of estimating the initial temperature of reservoir 34, $T_{Ri}$, and the temperature of the therapeutic fluid, $T_F$, respectively. The methods of FIGS. 11 and 12 are, generally speaking, examples of a method including sensing a pressure of a reservoir of a fluid delivery device using a pressure sensor, and estimating a temperature related to adding a therapeutic fluid to or removing the fluid from the reservoir based on the sensed pressure.

The example method of FIG. 12 includes sensing a pressure of a reservoir of a fluid delivery device using a pressure sensor (300), identifying a pressure at which a first derivative of the sensed pressure with respect to time traverses a first threshold as the therapeutic fluid is removed from the reservoir (302), and determining an initial temperature of the reservoir at the identified pressure of the reservoir based on a temperature-pressure characteristic for the fluid delivery device as the therapeutic fluid is removed from the reservoir (304). Similarly, the example method of FIG. 13 includes sensing a pressure of a reservoir of a fluid delivery device using a pressure sensor (310) identifying a local maximum pressure of the reservoir as the therapeutic fluid is added (312), determining a first temperature of the reservoir at the identified local maximum pressure of the reservoir based on a temperature-pressure characteristic for the fluid delivery device as the therapeutic fluid is added to the reservoir (314), and calculating a temperature of the therapeutic fluid based on the initial and first temperatures of the reservoir (316).

Identifying a pressure at which a first derivative of the sensed pressure with respect to time traverses a first threshold as the therapeutic fluid is removed from the reservoir (302), and determining an initial temperature of the reservoir, $T_{Ri}$, at the identified pressure of the reservoir based on a temperature-pressure characteristic for the fluid delivery device as the therapeutic fluid is removed from the reservoir (304) in the example method of FIG. 12, may be accomplished by employing techniques similar to those described above with reference to the method of FIG. 4 and the pressure, volume, and temperature characteristics of IMD 12 illustrated in FIGS. 5-9. Similarly, identifying a local maximum pressure of the reservoir as the therapeutic fluid is added to reservoir 34 (312), determining a first temperature of the reservoir, $T_{R1}$, at the identified local maximum pressure of the reservoir based on a temperature-pressure characteristic for the fluid delivery device as the therapeutic fluid is added to the reservoir (314), and calculating a temperature of the therapeutic fluid, $T_F$, based on the initial and first temperatures of the reservoir (316) in the example method of FIG. 13 may be accomplished by employing techniques similar to those described above with reference to the method of FIG. 4 and the pressure, volume, and temperature characteristics of IMD 12 illustrated in FIGS. 5-9.

Although the examples methods of FIGS. 12 and 13 have been described with reference to sensing the pressure of reservoir 34 of IMD 12, other pressures within the device may be sensed and employed in the foregoing temperature estimation methods. In particular, for example, pressure sensor 42 of IMD 12 may sense the pressure somewhere in refill port assembly 36, including, e.g., in chamber 48 of the refill port assembly.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
   sensing a pressure within a fluid delivery device using a pressure sensor as a therapeutic fluid is added to or removed from a reservoir of the device;
   estimating a pressure of the reservoir based on the sensed pressure, an estimated initial temperature of the reservoir as the therapeutic fluid is added or removed based on the sensed pressure, and an estimated temperature of the therapeutic fluid based on the sensed pressure, wherein the estimated pressure of the reservoir is different than the sensed pressure; and
   determining, by a processor, a volume of the fluid added to or removed from the reservoir based on the sensed pressure and the estimated pressure of the reservoir.

2. The method of claim 1, further comprising combining the fluid volume added to or removed from the reservoir with a starting volume of therapeutic fluid in the reservoir to determine a fill status of the reservoir.

3. The method of claim 2, wherein the fill status of reservoir comprises one of a volume of therapeutic fluid in the reservoir, an indication that the reservoir is empty, an indication that the reservoir is being filled, or an indication that the reservoir is full.

4. The method of claim 2, further comprising determining the starting volume by subtracting a volume of the therapeutic fluid pumped from the fluid delivery device since a time at which the reservoir was last full from a volume of the therapeutic fluid in the reservoir when the reservoir was last full.

5. The method of claim 4, further comprising determining the volume of therapeutic fluid pumped from the fluid delivery device by multiplying a number of strokes of a pump of the fluid delivery device by a volume of fluid pumped per stroke.

6. The method of claim 2, further comprising displaying the fill status of the reservoir.

7. The method of claim 2, further comprising generating an alarm based on the fill status of the reservoir.

8. The method of claim 1, further comprising:
estimating the initial temperature of the reservoir as the therapeutic fluid is added or removed based on the sensed pressure; and
estimating the temperature of the therapeutic fluid based on the sensed pressure.

9. The method of claim 8, wherein estimating the initial temperature of the reservoir comprises:
identifying a pressure at which a first derivative of the sensed pressure with respect to time traverses a first threshold as the therapeutic fluid is added to or removed from the reservoir; and
determining an initial temperature of the reservoir at the identified pressure of the reservoir based on a temperature-pressure characteristic for the fluid delivery device as the therapeutic fluid is added to or removed from the reservoir.

10. The method of claim 9, wherein estimating the temperature of the therapeutic fluid comprises:
identifying a local maximum pressure of the reservoir as the therapeutic fluid is added or removed;
determining a first temperature of the reservoir at the identified local maximum pressure of the reservoir based on a temperature-pressure characteristic for the fluid delivery device as the therapeutic fluid is added to or removed from the reservoir; and
calculating a temperature of the therapeutic fluid based on the initial and first temperatures of the reservoir.

11. The method of claim 10, wherein identifying a local maximum pressure of the reservoir comprises at least one of:
determining that a first derivative of the sensed pressure with respect to time traverses a second threshold as the therapeutic fluid is added to or removed from the reservoir;
determining that a difference between a first pressure of the reservoir and a second pressure of the reservoir sensed using the pressure sensor traverses a third threshold; or
determining an amount of time since a change in a local maximum pressure of the reservoir sensed using the pressure sensor has traversed a fourth threshold.

12. The method of claim 10, wherein the first threshold is a negative pressure differential and the second threshold is a positive pressure differential.

13. The method of claim 1, wherein:
sensing the pressure within the fluid delivery device using the pressure sensor comprises sensing a pressure within a refill port assembly of the fluid delivery device using the pressure sensor; and
estimating the pressure of the reservoir comprises estimating, based on the sensed pressure within the refill port assembly, the pressure of the reservoir.

14. The method of claim 13, wherein determining a volume of fluid added to or removed from the reservoir based on the sensed pressure and the estimated pressure of the reservoir comprises:
calculating a difference between the sensed pressure and the estimated pressure of the reservoir;
calculating a rate at which the therapeutic fluid is added to or removed from the reservoir based on the difference between the sensed pressure and the estimated pressure of the reservoir and a known fluidic restriction constant for the fluid delivery device; and
determining a volume of fluid added to or removed from the reservoir by integrating the fluid rate over a time during which the fluid is added or removed.

15. The method of claim 14, wherein the fluid rate is positive when fluid is being added to the reservoir and negative when fluid is being removed from the reservoir.

16. The method of claim 1, wherein sensing the pressure within the fluid delivery device using a pressure sensor comprises sensing a pressure within the reservoir using a pressure sensor.

17. The method of claim 16, wherein determining a volume of fluid added to or removed from the reservoir based on the sensed pressure and the estimated pressure of the reservoir comprises:
calculating a difference between the sensed pressure and the estimated pressure of the reservoir; and
determining a volume of fluid added to or removed from the reservoir by multiplying the difference between the sensed pressure and the estimated pressure of the reservoir by a pressure sensitivity to volume changes constant for the reservoir.

18. A fluid delivery system comprising:
an implantable fluid delivery device comprising:
a reservoir configured to store a therapeutic fluid;
a pressure sensor configured to sense one or more pressures within the fluid delivery device; and
a processor configured to sense a pressure within the fluid delivery device using the pressure sensor as a therapeutic fluid is added to or removed from the reservoir, estimate a pressure of the reservoir based on the sensed pressure, an estimated initial temperature of the reservoir as the therapeutic fluid is added or removed based on the sensed pressure, and an estimated temperature of the therapeutic fluid based on the sensed pressure, wherein the estimated pressure of the reservoir is different than the sensed pressure, and determine a volume of the fluid added to or removed from the reservoir based on the sensed pressure and the estimated pressure of the reservoir.

19. The system of claim 18, wherein the implantable fluid delivery device comprises the processor.

20. The system of claim 18, further comprising a programmer that comprises the processor, wherein the programmer is configured to program the fluid delivery device.

21. The system of claim 18, wherein the processor is configured to combine the fluid volume added to or removed from the reservoir with a starting volume of therapeutic fluid in the reservoir to determine a fill status of the reservoir.

22. The system of claim 21, wherein the fill status of reservoir comprises one of a volume of therapeutic fluid in the reservoir, an indication that the reservoir is empty, an indication that the reservoir is being filled, or an indication that the reservoir is full.

23. The system of claim 21, wherein the processor is configured to determine the starting volume by subtracting a volume of the therapeutic fluid pumped from the fluid delivery device since a time at which the reservoir was last full from a volume of the therapeutic fluid in the reservoir when the reservoir was last full.

24. The system of claim 23, wherein the processor is configured to determine the volume of therapeutic fluid pumped from the fluid delivery device by multiplying a number of strokes of a pump of the fluid delivery device by a volume of fluid pumped per stroke.

25. The system of claim 21, wherein the processor is configured to display the fill status of the reservoir.

26. The system of claim 21, wherein the processor is configured to generate an alarm based on the fill status of the reservoir.

27. The system of claim 18, wherein the processor is configured to estimate:
   estimate the initial temperature of the reservoir as the therapeutic fluid is added or removed based on the sensed pressure; and
   estimate the temperature of the therapeutic fluid based on the sensed pressure.

28. The system of claim 18, wherein the processor is configured to estimate the initial temperature of the reservoir by at least:
   identifying a pressure at which a first derivative of the sensed pressure with respect to time traverses a first threshold as the therapeutic fluid is added to or removed from the reservoir; and
   determining an initial temperature of the reservoir at the identified pressure of the reservoir based on a temperature-pressure characteristic for the fluid delivery device as the therapeutic fluid is added to or removed from the reservoir.

29. The system of claim 28, wherein the processor is configured to estimate the temperature of the therapeutic fluid by at least:
   identifying a local maximum pressure of the reservoir as the therapeutic fluid is added or removed;
   determining a first temperature of the reservoir at the identified local maximum pressure of the reservoir based on a temperature-pressure characteristic for the fluid delivery device as the therapeutic fluid is added to or removed from the reservoir; and
   calculating a temperature of the therapeutic fluid based on the initial and first temperatures of the reservoir.

30. The system of claim 29, wherein the processor is configured to identify a local maximum pressure of the reservoir by at least one of:
   determining that a first derivative of the sensed pressure with respect to time traverses a second threshold as the therapeutic fluid is added to or removed from the reservoir;
   determining that a difference between a first pressure of the reservoir and a second pressure of the reservoir sensed using the pressure sensor traverses a third threshold; or
   determining an amount of time since a change in a local maximum pressure of the reservoir sensed using the pressure sensor has traversed a fourth threshold.

31. The system of claim 29, wherein the first threshold is a negative pressure differential and the second threshold is a positive pressure differential.

32. The system of claim 18, wherein the processor is configured to sense the pressure within a refill port assembly of the fluid delivery device using the pressure sensor, and wherein the processor is configured to estimate, based on the sensed pressure within the refill port assembly, the pressure of the reservoir.

33. The system of claim 32, wherein the processor is configured to determine a volume of fluid added to or removed from the reservoir based on the sensed pressure and the estimated pressure of the reservoir at least by:
   calculating a difference between the sensed pressure and the estimated pressure of the reservoir;
   calculating a rate at which the therapeutic fluid is added to or removed from the reservoir based on the difference between the sensed pressure and the estimated pressure of the reservoir and a known fluidic restriction constant for the fluid delivery device; and
   determining a volume of fluid added to or removed from the reservoir by integrating the fluid rate over a time during which the fluid is added or removed.

34. The system of claim 33, wherein the fluid rate is positive when fluid is being added to the reservoir and negative when fluid is being removed from the reservoir.

35. The system of claim 18, wherein the processor is configured to sense a pressure within the reservoir using the pressure sensor.

36. The system of claim 35, wherein the processor is configured to determine the volume of fluid added to or removed from the reservoir based on the sensed pressure and the estimated pressure of the reservoir by at least:
   calculating a difference between the sensed pressure and the estimated pressure of the reservoir; and
   determining the volume of fluid added to or removed from the reservoir by multiplying the difference between the sensed pressure and the estimated pressure of the reservoir by a pressure sensitivity to volume changes constant for the reservoir.

37. A non-transitory computer-readable storage medium comprising instructions for causing a programmable processor in an implantable fluid delivery system to:
   receive a pressure within a fluid delivery device from a pressure sensor as a therapeutic fluid is added to or removed from a reservoir of the device;
   estimate a pressure of the reservoir based on the sensed pressure, an estimated initial temperature of the reservoir as the therapeutic fluid is added or removed based on the sensed pressure, and an estimated temperature of the therapeutic fluid based on the sensed pressure, wherein the estimated pressure of the reservoir is different than the sensed pressure; and
   determine a volume of the fluid added to or removed from the reservoir based on the sensed pressure and the estimated pressure of the reservoir.

38. A system comprising:
   means for sensing a pressure within a fluid delivery device using a pressure sensor as a therapeutic fluid is added to or removed from a reservoir of the device;
   means for estimating a pressure of the reservoir based on the sensed pressure, an estimated initial temperature of the reservoir as the therapeutic fluid is added or removed based on the sensed pressure, and an estimated temperature of the therapeutic fluid based on the sensed pressure, wherein the estimated pressure of the reservoir is different than the sensed pressure; and means for determining a volume of the fluid added to or removed from the reservoir based on the sensed pressure and the estimated pressure of the reservoir.

39. A method comprising:

sensing a pressure within a fluid delivery device using a pressure sensor as a therapeutic fluid is added to or removed from a reservoir of the device;

estimating an initial temperature of the reservoir as the therapeutic fluid is added or removed based on the sensed pressure;

estimating a temperature of the therapeutic fluid based on the sensed pressure;

determining an estimated pressure of the reservoir based on the estimated initial temperature of the reservoir and the estimated temperature of the therapeutic fluid, wherein the estimated pressure of the reservoir is different than the sensed pressure; and determining, by a processor, a volume of the fluid added to or removed from the reservoir based on the sensed pressure and the estimated pressure of the reservoir.

* * * * *